United States Patent
Hsu et al.

(10) Patent No.: US 11,773,205 B2
(45) Date of Patent: Oct. 3, 2023

(54) CROSSLINKING AGENT, PREPARATION PROCESS AND USES THEREOF, HYDROGEL AND BIODEGRADABLE CRYOGEL COMPRISING CROSSLINKING AGENT

(71) Applicant: National Taiwan University, Taipei (TW)

(72) Inventors: Shan-hui Hsu, Taipei (TW); Tzu-Wei Lin, Taipei (TW)

(73) Assignee: NATIONAL TAIWAN UNIVERSITY, Taipei (TW)

(*) Notice: Subject to any disclaimer, the term of this patent is extended or adjusted under 35 U.S.C. 154(b) by 20 days.

(21) Appl. No.: 16/998,652

(22) Filed: Aug. 20, 2020

(65) Prior Publication Data

US 2022/0056192 A1  Feb. 24, 2022

(51) Int. Cl.
| | |
|---|---|
| A61K 31/785 | (2006.01) |
| A61K 9/00 | (2006.01) |
| C08G 18/42 | (2006.01) |
| C12N 5/0786 | (2010.01) |
| C08G 18/75 | (2006.01) |
| A61K 9/06 | (2006.01) |
| C08K 5/07 | (2006.01) |

(52) U.S. Cl.
CPC ........ *C08G 18/4286* (2013.01); *A61K 9/0019* (2013.01); *A61K 9/06* (2013.01); *A61K 31/785* (2013.01); *C08G 18/755* (2013.01); *C08K 5/07* (2013.01); *C12N 5/0645* (2013.01)

(58) Field of Classification Search
None
See application file for complete search history.

(56) References Cited

U.S. PATENT DOCUMENTS

| | | | | |
|---|---|---|---|---|
| 2011/0195242 | A1* | 8/2011 | Burckhardt | C08G 18/36 428/221 |
| 2011/0262489 | A1* | 10/2011 | Zhao | A61K 9/0021 424/400 |
| 2011/0286925 | A1* | 11/2011 | Lerouge | A61L 24/08 424/9.1 |
| 2021/0361570 | A1* | 11/2021 | Hoare | A61K 47/36 |

OTHER PUBLICATIONS

Shih-Hsiang Hsiao and Shan-hui Hsu. "Synthesis and Characterization of Dual Stimuli-Sensitive Biodegradable Polyurethane Soft Hydrogels for 3D Cell-Laden Bioprinting." ACS Applied Materials & Interfaces, vol. 10, 2018, pp. 29273-29287. (Year: 2018).*
Junpeng Xu, Yi Liu. and Shan-hui Hsu. "Hydrogels Based on Schiff Base Linkages for Biomedical Applications." Molecules, vol. 24, 2019, pp. 1-21, published Aug. 19, 2019. (Year: 2019).*
Tian Qin et al. "Dopamine induces growth inhibition and vascular normalization through reprogramming M2-polarized macrophages in rat C6 glioma." Toxicology and Applied Pharmacology, vol. 286 (2015), pp. 112-123. (Year: 2015).*

(Continued)

*Primary Examiner* — Isaac Shomer
(74) *Attorney, Agent, or Firm* — Muncy, Geissler, Olds & Lowe, P.C.

(57) ABSTRACT

The present disclosure provides a crosslinking agent, the preparation process and uses thereof, a hydrogel and a biodegradable cryogel including the crosslinking agent.

8 Claims, 30 Drawing Sheets

(56) References Cited

OTHER PUBLICATIONS

Lin, Tzu-Wei et al., "Self-Healing Hydrogels and Cryogels from Biodegradable Polyurethane Nanoparticle Crosslinked Chitosan" Advanced Science, vol. 7, Issue No. 3, 2020, 1901388, 13 pages.
Tsai-Yu Chen et al., "Cryogel/hydrogel biomaterials and acupuncture combined to promote diabetic skin wound healing through immunomodulation", Biomaterials journal 269 (2021) 120608: www.elsevier.com/locate/biomaterials, pp. 1-16.
Junpeng Xu et al., "An anti-inflammatory electroconductive hydrogel with self-healing property for the treatment of Parkinson's disease", Chemical Engineering Journal 446 (2022) 137180: www.elsevier.com/locate/cej, pp. 1-14.

\* cited by examiner

CROSSLINKING AGENT, PREPARATION PROCESS AND USES THEREOF, HYDROGEL AND BIODEGRADABLE CRYOGEL COMPRISING CROSSLINKING AGENT

BACKGROUND OF THE INVENTION

1. Field of the Invention

The present invention relates to a crosslinking agent, the preparation process and uses thereof, a hydrogel and a biodegradable cryogel comprising the crosslinking agent.

2. The Prior Art

Hydrogel is a polymer material with a three-dimensional network structure prepared by physical or chemical crosslinking, which uses water as a dispersion medium, can absorb a large amount of water to swell and maintain its structural stability. As a material with high water absorption and high water retention, hydrogel has been widely used in the fields of industry, agriculture and biological tissue engineering. However, in practical applications, the traditional hydrogels are subjected to external forces, light, heat, and chemistry alone or in combination, which may cause micro-cracks that are difficult to detect and repair. The expansion and increase of these micro-cracks will reduce the mechanical properties of the material, shorten its service life, and bring serious hidden dangers to the use of the material.

In addition, the hydrogel can be used as a dressing, which can absorb a large amount of exudate, promote self-debridement of the wound surface, maintain a moderate humidity environment on the wound surface, and accelerate wound healing. However, the oxygen permeability of traditional hydrogels is generally poor. When the wound is covered for a long time, it may make the wound surface feel sultry and burning, increase the discomfort of the patient, and is not conducive to wound healing. In addition, the traditional hydrogel has the disadvantages of cytotoxicity, slow response rate to the environment, unfavorable drug release, complicated manufacturing process, and difficulty in mass production.

In order to solve the above problems, those skilled in the art urgently need to develop a crosslinking agent with high biocompatibility, adjustable biodegradation rate, no cytotoxicity, simple process, benefit to mass production, environmental protection, environmental responsiveness and drug release, self-healing and injectable properties, the preparation process thereof, a hydrogel and a biodegradable cryogel comprising the crosslinking agent for the benefit of a large group of people in need thereof.

SUMMARY OF THE INVENTION

A primary objective of the present invention is to provide a crosslinking agent, comprising a plurality of polyurethane (PU) nanoparticles, wherein each of the polyurethane nanoparticles has a plurality of aldehyde groups.

According to an embodiment of the present invention, each of the polyurethane nanoparticles has a particle diameter between 10 and 150 nm.

According to an embodiment of the present invention, each of the polyurethane nanoparticles is self-assembled from multiple polyurethane molecules, and each polyurethane molecule has weight average molecular weight of $1.33 \times 10^5$ Da.

Another objective of the present invention is to provide a biodegradable cryogel, comprising the aforementioned crosslinking agent, wherein the biodegradable cryogel is obtained by reacting the crosslinking agent with a polymer having an amine group and being placed at a temperature of −17° C. to −25° C.

According to an embodiment of the present invention, the biodegradable cryogel is prepared by a 3D printing method.

According to an embodiment of the present invention, the biodegradable cryogel is injectable.

Another objective of the present invention is to provide a method for regulating biodegradation rate, comprising administering to a subject in need thereof the aforementioned crosslinking agent.

Another objective of the present invention is to provide a method for preparing the aforementioned crosslinking agent, comprising the following steps: (a) performing a first stirring treatment on polycaprolactone diol or a mixture of the polycaprolactone diol and a second diol, so that the polycaprolactone diol or the mixture of the polycaprolactone diol and the second diol presents a homogeneous liquid; (b) performing a catalytic reaction on the polycaprolactone diol or the mixture of the polycaprolactone diol and the second diol; (c) adding dimethylol propionic acid and butanone and performing a first reaction, followed by adding triethylamine and performing a second reaction to obtain a product; and (d) performing a second stirring treatment on the product, followed by adding a first chain extender and a second chain extender and performing a chain extension reaction to obtain the crosslinking agent.

According to an embodiment of the present invention, the first chain extender is ethylene diamine.

According to an embodiment of the present invention, the second chain extender is glyoxal.

According to an embodiment of the present invention, the second diol is polyethylene butylene adipate diol (PEBA diol), poly(L-lactide) (PLLA) diol, or poly(D,L-lactide) (PDLLA) diol.

Another objective of the present invention is to provide a method for regulating biodegradation rate of a hydrogel, comprising administering to a subject in need thereof a crosslinking agent prepared by the aforementioned method.

Another objective of the present invention is to provide a hydrogel, comprising the aforementioned crosslinking agent, wherein the hydrogel is obtained by reacting the crosslinking agent with a polymer having an amine group.

According to an embodiment of the present invention, the polymer having the amine group is glycol chitosan or N-carboxyethyl chitosan.

According to an embodiment of the present invention, the hydrogel has a self-healing property.

According to an embodiment of the present invention, the hydrogel is a cryogel, wherein the cryogel is obtained by reacting the crosslinking agent with the polymer having the amine group and being placed at a temperature of −17° C. to −25° C.

According to an embodiment of the present invention, the cryogel has a shape memory property.

According to an embodiment of the present invention, the cryogel is injectable.

According to an embodiment of the present invention, the cryogel is used to culture cells, is biocompatible, and has a property of regulating proportion of M2 macrophages.

In summary, the biodegradable cryogel has the effect on high biocompatibility, adjustable biodegradation rate, no cytotoxicity, simple process, benefit to mass production, environmental protection, environmental responsiveness and drug release, and having self-healing, injectable and shape memory properties.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

In the context, PCL diol represents polycaprolactone diol, EB represents PEBA diol (polyethylene butylene adipate diol), PU represents polyurethane, PU NP represents the polyurethane nanoparticle, GC or CS represents glycol chitosan, and DFPU represents the crosslinking agent.

Example 1

Figure 1A:
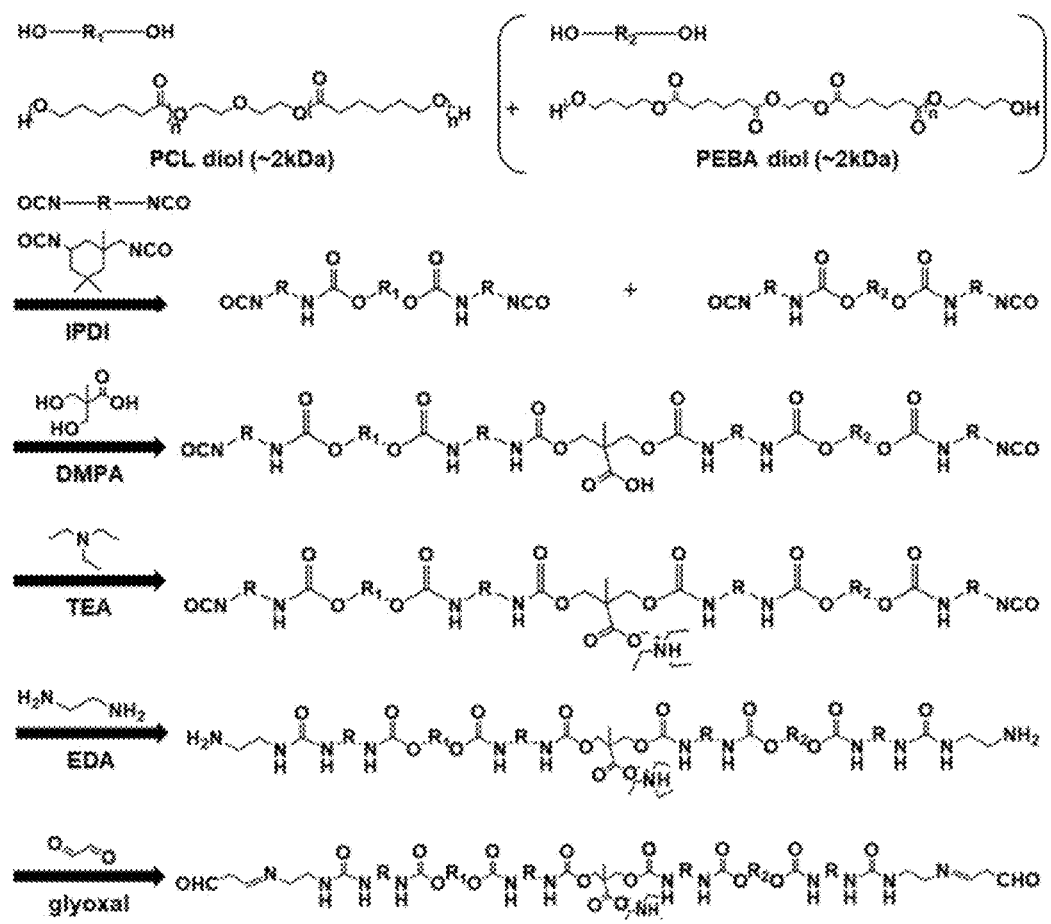
FIG. 1A is a preparation flow chart of the crosslinking agent of the present invention.

Preparation of Crosslinking Agent, Degradable Hydrogel Comprising Crosslinking Agent and Cryogel, and Analysis of Attenuated Total Reflectance Fourier-Transform Infrared Spectroscopy (ATR-FTIR) of Crosslinking Agent 1.1 Preparation of Crosslinking Agent and ATR-FTIR Analysis First, the polycaprolactone diol (PCL diol) and polyethylene butylene adipate diol (PEBA diol) (or PCL diol only) were added to the four-necked reaction flask, and the pre-polymerization temperature was adjusted to of 75-80° C., followed by mixing evenly with a mechanical stirring speed between 150-180 rpm, so that the PCL diol presents a homogeneous liquid. In another embodiment of the present invention, PEBA diol can be replaced with poly(L-lactide) (PLLA) diol or poly(D,L-lactide) (PDLLA) diol. The catalyst (stannous octoate) and isophorone diisocyanate (IPDI) were added to catalyze the PCL diol for 3 hours. The dimethylol propionic acid (DMPA) and butanone were added to the reaction flask and the reaction was performed for 1 hour, the temperature was cooled to 50° C., followed by adding triethylamine (TEA) for neutralization reaction for 0.5 hour. After the reaction was completed, the temperature was lowered to 45° C., stirring was performed at a stirring speed of 1100 rpm, and secondary distilled water was quickly added. After the water was dispersed, the first chain extender (ethylene diamine, EDA) diluted with water was added and reaction was performed for 1 hour to obtain the polyurethane nanoparticle (PU NP), and the second chain extender (glyoxal) diluted with water was added, followed by reacting for 0.5 hour to obtain the crosslinking agent of the present invention. The preparation process of the crosslinking agent of the present invention is shown in FIG. 1A.

Figure 1B:
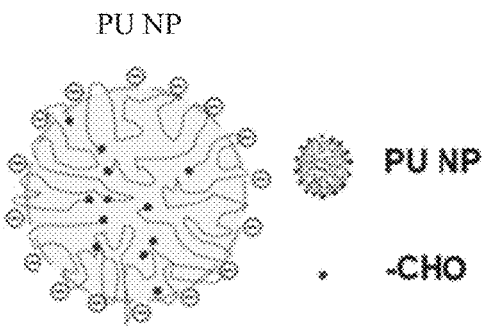
FIG. 1B is a schematic diagram showing the structure of the crosslinking agent of the present invention.

The crosslinking agent of the present invention comprises polyurethane nanoparticles, wherein each of the polyurethane nanoparticles has a plurality of aldehyde groups (—CHO). The structure diagram of the crosslinking agent of the present invention is shown in FIG. 1B, wherein PU NP represents the polyurethane nanoparticle.

Figure 1C:
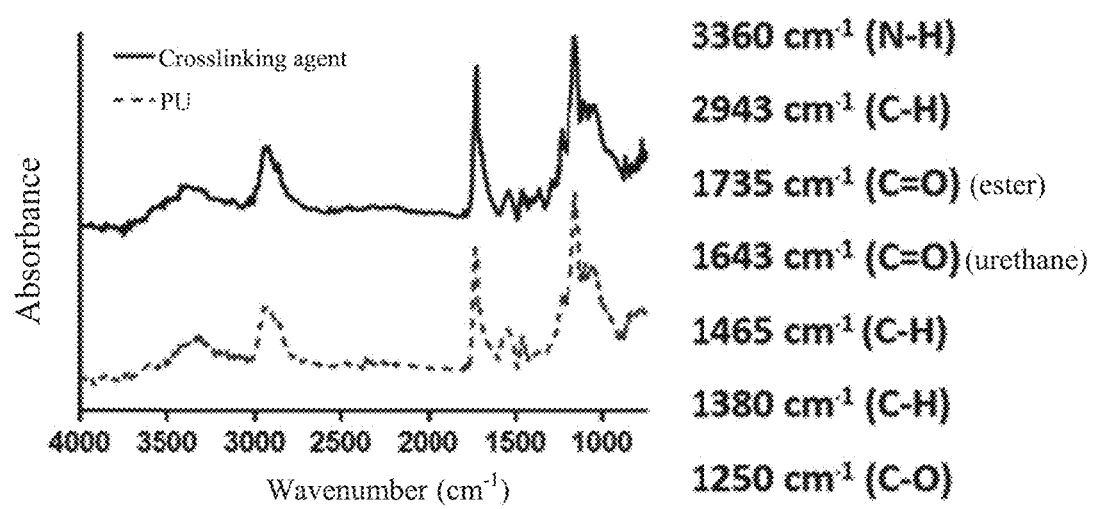
FIG. 1C is an analysis diagram of the attenuated total reflectance Fourier-transform infrared spectroscopy (ATR-FTIR) of the crosslinking agent of the present invention.

In addition, the crosslinking agent of the present invention is modified from polyurethane (PU). Through ATR-FTIR (spectrum 100 model, Perkin Elmer) analysis, it can be proved that the crosslinking agent was modified by linking specific functional group. The ATR-FTIR analysis diagram of the crosslinking agent is shown in FIG. 1C, wherein PU represents polyurethane.

1.2 Preparation of Degradable Hydrogel and Cryogel

The preparation process of the degradable hydrogel is as follows: the crosslinking agent obtained above was mixed at room temperature (for example, 25° C. to 37° C.) with a polymer having an amine group in a specific ratio (fixed glycol chitosan accounts for 2% of the total solid content, and the crosslinking agent accounts for 1.7±0.3% of the total solid content) to obtain the degradable hydrogel of the present invention. In an embodiment of the present invention, the polymer having an amine group is preferably glycol chitosan.

Figure 2:
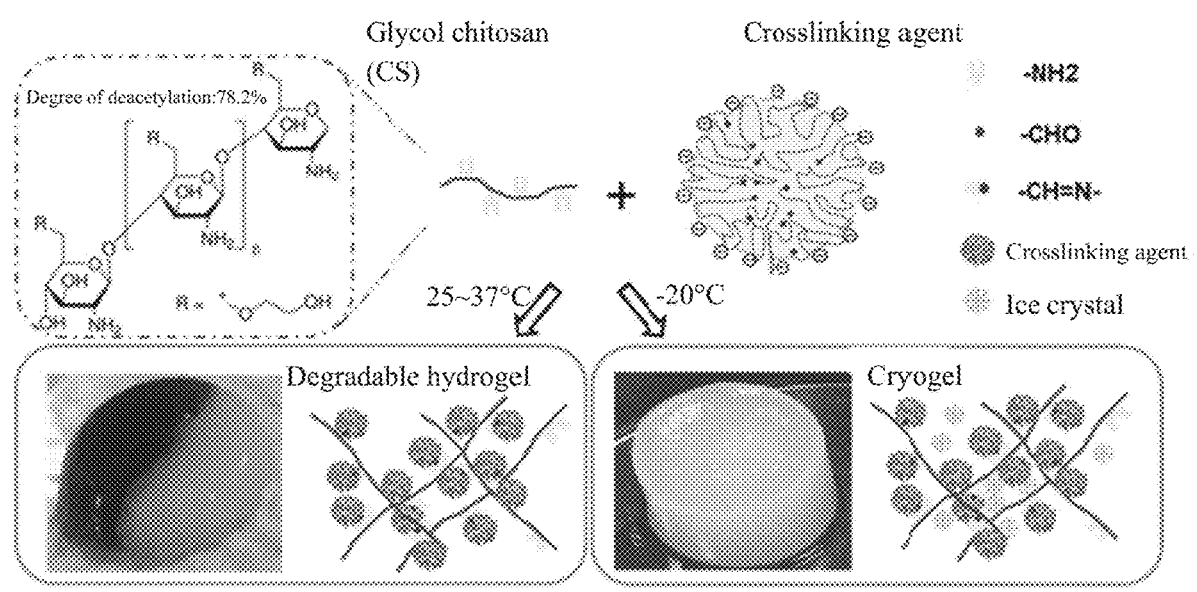
FIG. 2 is a schematic diagram of preparation of the degradable hydrogel and cryogel of the present invention.

The preparation process of the cryogel is as follows: the crosslinking agent obtained above and the polymer having an amine group (i.e., glycol chitosan) were mixed at a low temperature (−17° C. to −25° C.) at the above-mentioned specific ratio to obtain the cryogel of the present invention after thawing. The schematic diagram of the preparation of the degradable hydrogel and the cryogel is shown in FIG. 2.

Example 2

Determination of Average Molecular Weight, Polydispersity (PDI), Zeta Potential and Particle Diameter of Crosslinking Agent In this example, the properties of the crosslinking agent, including the number average molecular weight (Mn, $10^5$ Da), weight average molecular weight (Mw, $10^5$ Da), polydispersity (PDI)(Mw/Mn), zeta potential (mV), and hydrodynamic diameter (nm), were measured at 25° C. through gel permeation chromatography (GPC) and dynamic light scattering (DLS).

TABLE 1

| Analyte | Mn ($*10^5$ Da) | Mw ($*10^5$ Da) | PDI (Mw/Mn) | zeta potential (mV) | hydrodynamic diameter (nm) |
|---|---|---|---|---|---|
| PU | 1.38 | 1.65 | 1.2 | −57.2 ± 0.4 | 36 ± 0.6 |
| Crosslinking agent | 0.90 | 1.33 | 1.5 | −51.4 ± 0.9 | 39.5 ± 9.6 |

It can be seen from Table 1 that PU is modified to form the crosslinking agent, and can form a stable dispersed suspension without precipitation (as can be seen from zeta potential), and other information is basic information before and after modification. In another embodiment of the invention, each of the polyurethane nanoparticles in the crosslinking agent has a particle diameter between 10 and 150 nm.

Example 3

Figure 3A:
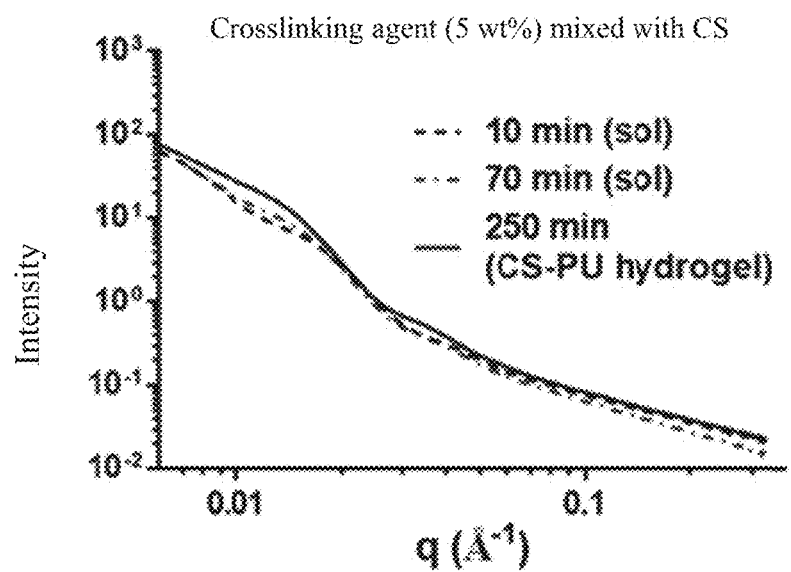
FIG. 3A is a data diagram showing the small-angle X-ray scattering test of the degradable hydrogel of the present invention.
Figure 3B:
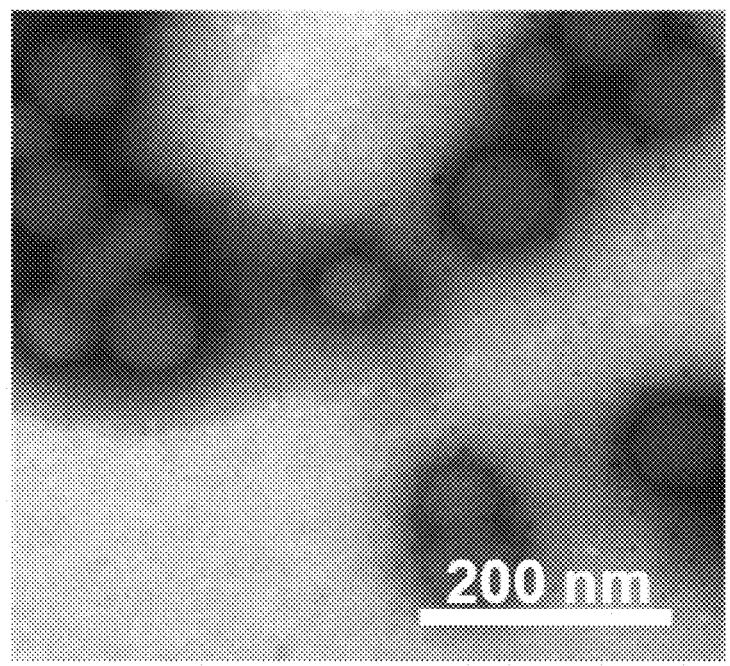
FIG. 3B is a transmission electron microscope analysis diagram of the crosslinking agent of the present invention.
Figure 3C:
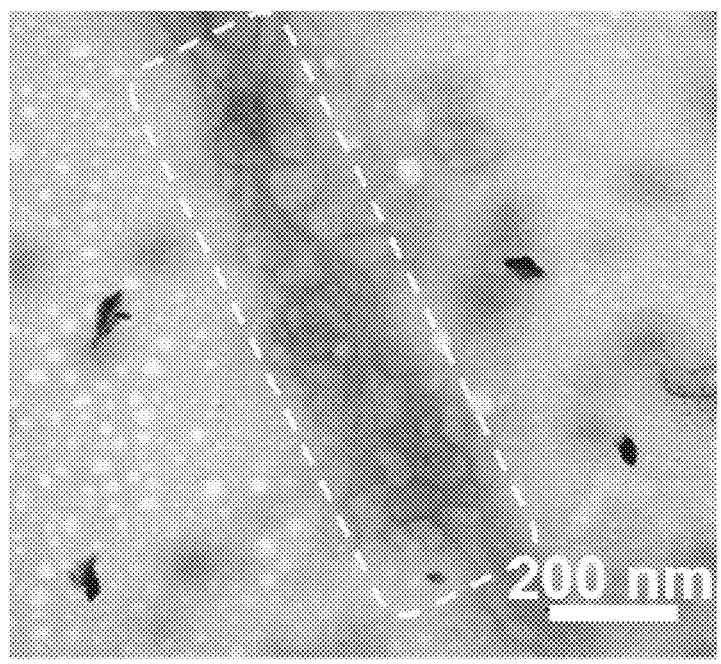
FIG. 3C is a transmission electron microscope analysis diagram showing the crosslinking agent of the present invention attached to glycol chitosan (GC).

Small-Angle X-Ray Scattering (SAXS) Test of Degradable Hydrogel and Transmission Electron Microscope (TEM) Analysis of Crosslinking Agent In this example, through small-angle X-ray scattering (SAXS), it is tested when the crosslinking agent forms a degradable hydrogel, there is a structural change near the size of polyurethane nanoparticles. The result is shown in FIG. 3A. In addition, this phenomenon can also be explained through transmission electron microscopy (TEM) analysis. The results are shown in FIGS. 3B and 3C.

FIG. 3A is a data diagram showing the small-angle X-ray scattering test of the degradable hydrogel of the present invention, wherein CS-PU hydrogel means a degradable hydrogel containing glycol chitosan and polyurethane. It can be seen from FIG. 3A that the peak has changed with time over 0.01 Å$^{-1}$, indicating that the structure has changed at this scale. It can be calculated to be about 40 nanometers by the formula, consistent with the particle size results of the nanoparticles of the crosslinking agent detected by DLS. Therefore, when the crosslinking agent forms a degradable hydrogel, there is a structural change near the size of the polyurethane nanoparticles. FIG. 3B is a transmission electron microscope analysis diagram of the crosslinking agent of the present invention. FIG. 3C is a transmission electron microscope analysis diagram showing the crosslinking agent of the present invention attached to glycol chitosan (GC). It can be seen from FIGS. 3B and 3C that the shape of the nanoparticles of the crosslinking agent has changed, so it can also help explain the phenomenon of structural changes near the size of the polyurethane nanoparticles when the crosslinking agent forms a degradable hydrogel.

Example 4

Gelation Mechanism and Optimal Ratio of Degradable Hydrogel

In this example, it was found that there was an unstable phenomenon when preparing the degradable hydrogel. Through hypothesis and repeated experiments, the optimal ratio was selected for subsequent experiments. The experimental process is as follows: the crosslinking agent and glycol chitosan with different ratios were selected to prepare a hydrogel and placed for observation. It was found through experiments that when fixed glycol chitosan accounts for 2% of the total solid content and the crosslinking agent accounts for <2% of the total solid content, the hydrogels remain stable after three days. While the crosslinking agent is an amount of <1.4%, gelation is too slow, and when the amount is >2%, the hydrogel shrinks and dehydrates in about three days. The results are shown in FIGS. 4A to 4C.

Figure 4A:
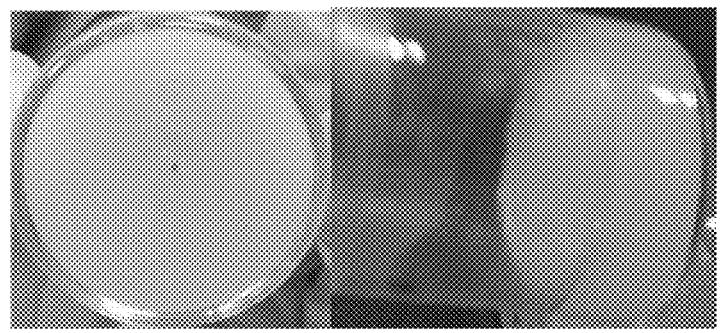
FIG. 4A is a schematic diagram of a degradable hydrogel formed by a high concentration of crosslinking agent.
Figure 4B:
FIG. 4B is a schematic diagram showing the phenomenon that the degradable hydrogel is deswelling after three days.
Figure 4C:
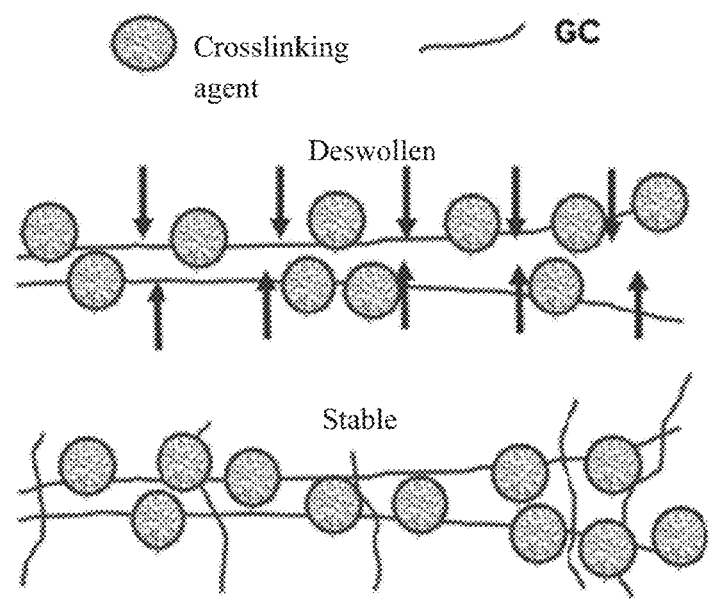
FIG. 4C is a schematic diagram of the gelation mechanism of the degradable hydrogel.

FIG. 4A is a schematic diagram of a degradable hydrogel formed by a high concentration (fixed glycol chitosan accounts for 2% of the total solid content and the crosslinking agent accounts for >2% of the total solid content) of crosslinking agent. FIG. 4B is a schematic diagram showing the phenomenon that the degradable hydrogel is deswelling after three days. FIG. 4C is a schematic diagram of the gelation mechanism of the degradable hydrogel. FIG. 4A shows a hydrogel with a high concentration ratio of crosslinking agent on day 0, and FIG. 4B shows a hydrogel with a high concentration ratio of crosslinking agent on day 3. It can be seen that the hydrogel shrinks and dehydrates on day 3, which is an unstable hydrogel. There are many aldehyde groups on the nanoparticles of the crosslinking agent, but the cross-linking rate with glycol chitosan is not the same, it will continue to cross-link after gelation, resulting in excessive cross-linking later, causing dehydration. An increase in the concentration of glycol chitosan (main chain) and a decrease in the concentration of the crosslinking agent can achieve an optimized stable structure, as shown in FIG. 4C. Therefore, there is an unstable phenomenon when preparing a degradable hydrogel.

The degradable hydrogel was subjected to component analysis to find the optimal composition ratio, wherein the best definition was that it could maintain shape for three days without shrinking or draining water. The result is shown in Table 2.

TABLE 2

| Composition ratio | Mass ratio of glycol chitosan (GC)/crosslinking agent/water | Mole ratio of —NH$_2$/—CHO/ H$_2$O | Total solid content (wt %) |
| --- | --- | --- | --- |
| 1.67% crosslinking agent/2% GC | 1:0.833:48.167 | 1:0.005:701.489 | 3.67 |

Example 5

Differential Scanning Calorimetry (DSC), Thermogravimetric Analysis (TGA) and X-Ray Diffraction (XRD) Analysis of Crosslinking Agent, Degradable Hydrogel and Cryogel In this example, thermogravimetric analysis (TGA) was used to observe the composition uniformity of the degradable hydrogel and cryogel of the present invention, and the difference in crystallization of PU and the crosslinking agent was observed through X-ray diffraction (XRD). The results are shown in FIGS. 5A and 5B.

Figure 5A:
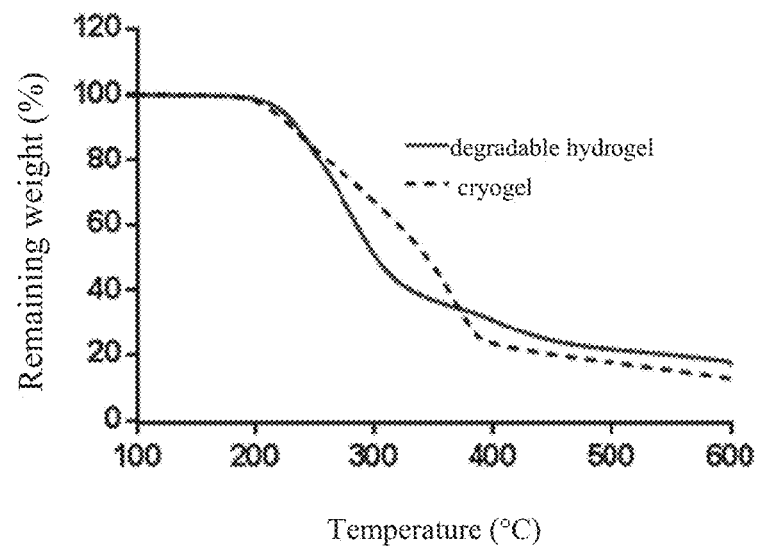
FIG. 5A is a thermogravimetric analysis (TGA) data diagram of the cryogel and degradable hydrogel of the present invention.
Figure 5B:
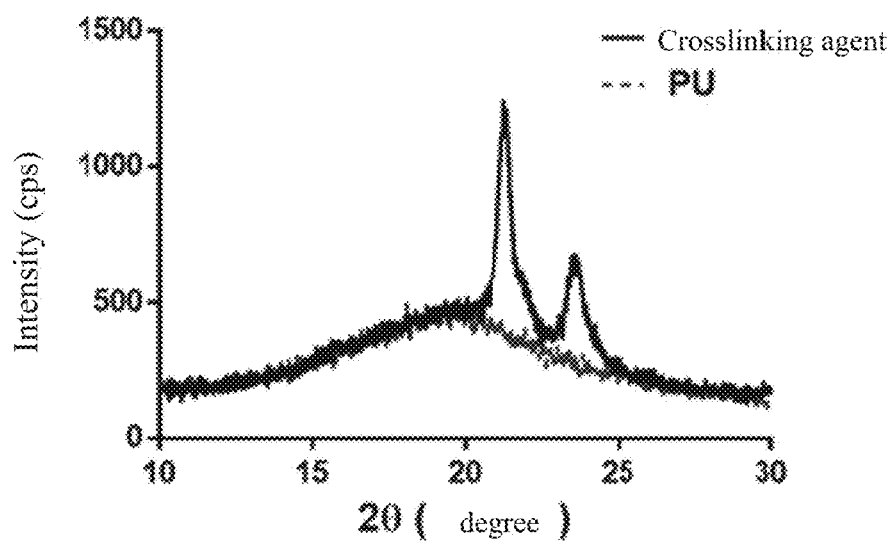
FIG. 5B is an X-ray diffraction (XRD) pattern of the crosslinking agent of the present invention and PU.

FIG. 5A is a thermogravimetric analysis (TGA) data diagram of the cryogel and degradable hydrogel of the present invention. It can be seen from FIG. 5A that the slope of the cryogel is gentler, which means that its composition is more non-uniform. FIG. 5B is an X-ray diffraction (XRD) pattern of the crosslinking agent of the present invention and PU. It can be seen from FIG. 5B that the crosslinking agent of the present invention has a crystalline difference from PU.

Example 6

Environmental Responsiveness of Degradable Hydrogel and Cryogel

In this example, the degradable hydrogel of the present invention is divided into two experimental groups (i.e., Experimental group 1 and Experimental group 2), wherein Experimental group 1 is added with 1 mL of 97% acetic acid, and Experimental group 2 is added 1 mL of aniline. The experimental results found that the degradable hydrogel in Experimental group 1 was liquefied within 5 minutes, and the degradable hydrogel in Experimental group 2 was liquefied after 48 hours.

Figure 6:
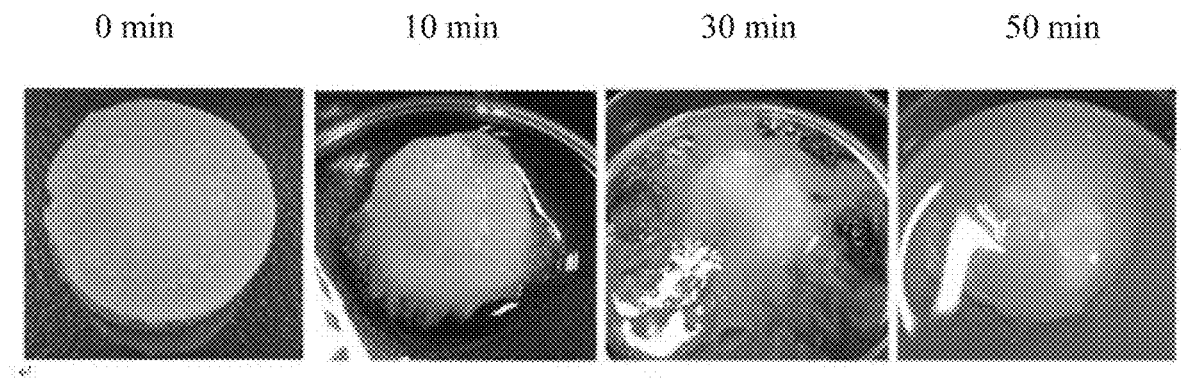
FIG. 6 is a schematic diagram of the environmental responsiveness of the cryogel of the present invention.

In addition, 1 mL of 97% acetic acid was added to the cryogel, it was found that the cryogel was liquefied within 50 minutes, as shown in FIG. 6. The results of this example confirm that the degradable hydrogel and cryogel of the present invention are environmentally responsive and have the potential to be used as drug release carriers. Furthermore, the composition of the degradable hydrogel and cryogel of the present invention are the same, only the process is different, and the substances that respond to the environment should have the same performance, only the time difference. The way of crosslinking is that the aldehyde group and the amine group form a Schiff base, which is acid sensitive. When encountering an amine molecule, the Schiff base is a dynamic covalent bond, and the amine molecule can compete with the amine group that originally forms the Schiff base. If the subsequent amine molecule has a single arm, how can the original cross-linked network be weakened when the bond is connected, resulting in the liquefaction of the hydrogel. If there is a benzene ring beside the amine molecule, the responsiveness is stronger and this phenomenon is more obvious. Therefore, the degradable hydrogel of the present invention is also responsive to amine group-containing molecules.

Example 7

Macroscopic Self-Healing Test of Degradable Hydrogel

Figure 7:
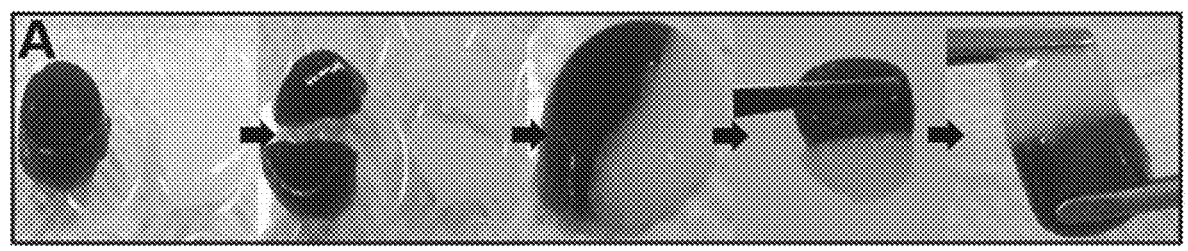
FIG. 7 is a macroscopic diagram of the degradable hydrogel of the present invention.

In this example, the macroscopic self-healing test was used to observe whether the degradable hydrogel of the present invention has self-healing properties. FIG. 7 is a macroscopic diagram of the degradable hydrogel of the present invention. As can be seen from FIG. 7, two groups of degradable hydrogels stained with trypan blue were prepared. Each group of degradable hydrogels was cut in half, and then different colors of degradable hydrogels were combined. After that, the healing of the merged junction was observed, and then it was found that the degradable hydrogel after healing can support its own weight without falling. When pulling, it can be seen that the two pieces have obviously healed into one piece, that is, the hydrogel can be healed after being placed for a period of time after it breaks, and it has recovered to a certain mechanical strength to support its own weight. The results of this example confirm that the degradable hydrogel of the present invention has good self-healing properties.

Example 8

Figure 8A:
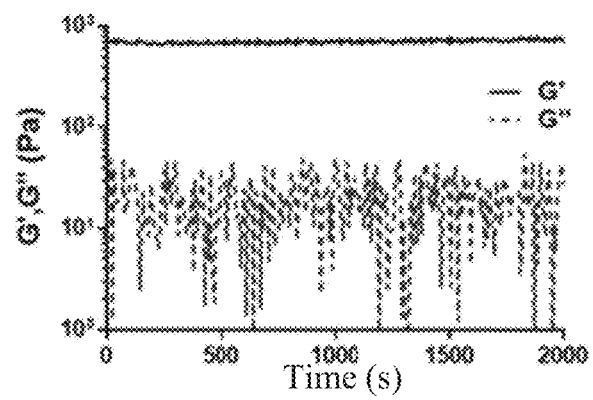
FIG. 8A is a diagram of the rheological properties of the degradable hydrogel of the present invention versus time.
Figure 8B:
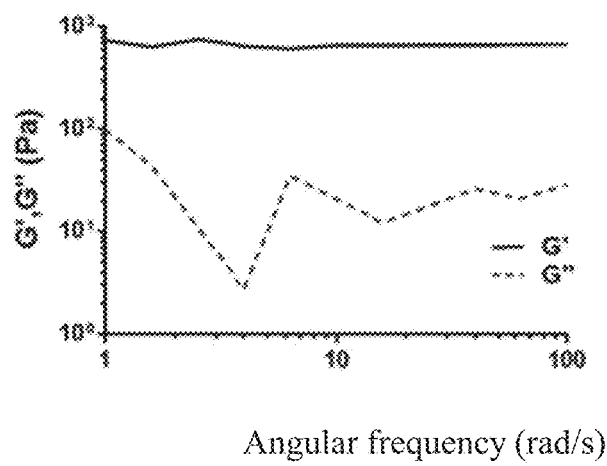
FIG. 8B is a diagram of the rheological properties of the degradable hydrogel of the present invention versus frequency.
Figure 8C:
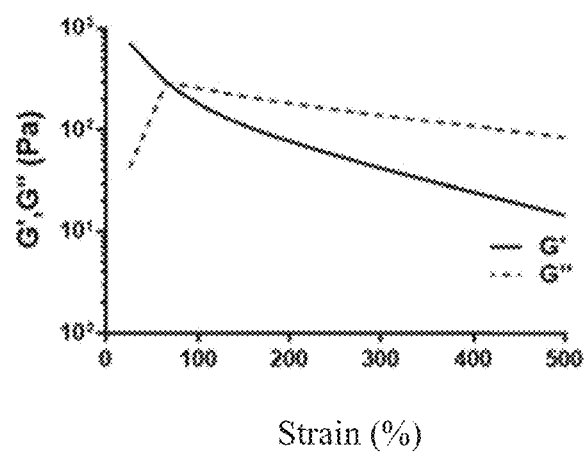
FIG. 8C is a diagram of the rheological properties of the degradable hydrogel of the present invention versus strain.
Figure 8D:
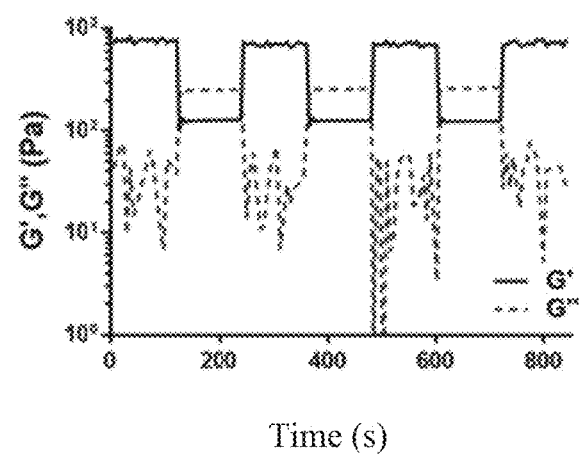
FIG. 8D is a microscopic self-healing test diagram of the degradable hydrogel of the present invention.
Figure 8E:
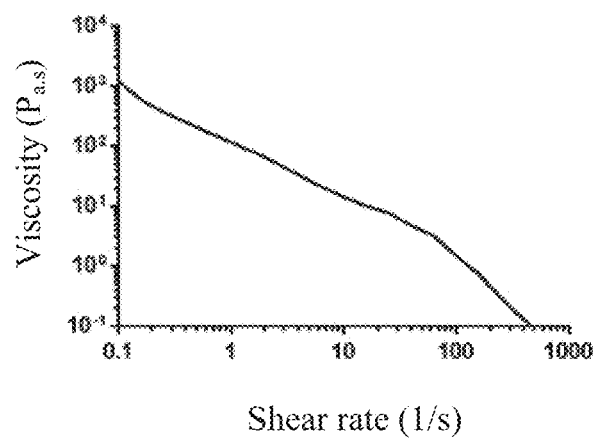
FIG. 8E is a diagram of the viscosity versus shear rate of the degradable hydrogel of the present invention.
Figure 8F:
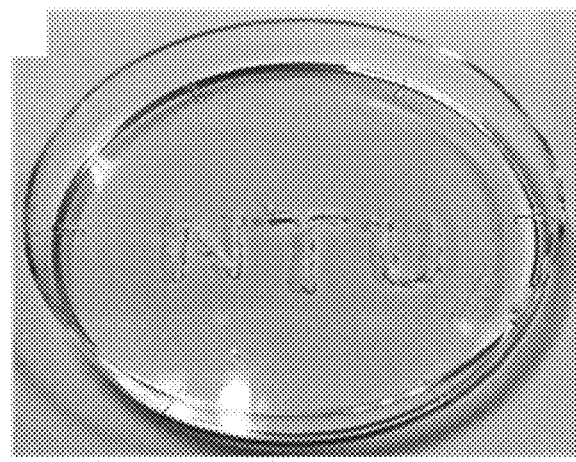
FIG. 8F is a test diagram showing the injectable properties of the degradable hydrogel of the present invention.

Analysis of Mechanical Properties and Microscopic Self-Healing Properties of Degradable Hydrogel In this example, the mechanical properties and microscopic self-healing properties of the degradable hydrogel of the present invention (solid content 28%) were analyzed at 37° C. through a rheometer. FIG. 8A is a diagram of the rheological properties of the degradable hydrogel of the present invention versus time. As can be seen from FIG. 8A, using the rheometer for time sweep, it can be seen that the mechanical property of the hydrogel is about 700 Pa. FIG. 8B is a diagram of the rheological properties of the degradable hydrogel of the present invention versus frequency. As can be seen from FIG. 8B, using the rheometer for frequency sweep, it can be seen that the hydrogel is still stable under different frequencies of shear. FIG. 8C is a diagram of the rheological properties of the degradable hydrogel of the present invention versus strain. It can be seen from FIG. 8C that using the rheometer for strain sweep, it can be seen that the hydrogel is destroyed when the strain is about 80%. FIG. 8D is a microscopic self-healing test diagram of the degradable hydrogel of the present invention. As can be seen from FIG. 8D, using the rheometer to perform the healing cycle, it can be seen that the hydrogel can heal itself and recover to close to the original mechanical strength after being destroyed, repeated many times. FIG. 8E is a diagram of the viscosity versus shear rate of the degradable hydrogel of the present invention. It can be seen from FIG. 8E that the static test with the rheometer can be seen as the shear rate increases, the viscosity of the hydrogel decreases, which is the characteristic of shear thinning, which is beneficial to the material can be applied to injection or 3D printing. FIG. 8F is a test diagram showing the injectable properties of the degradable hydrogel of the present invention. As can be seen from FIG. 8F, the degradable hydrogel of the present invention can be injected using a 26G needle (260 μm). The results of this example confirm that the degradable hydrogel of the present invention has good self-healing and injectable properties.

Example 9

Figure 9A:
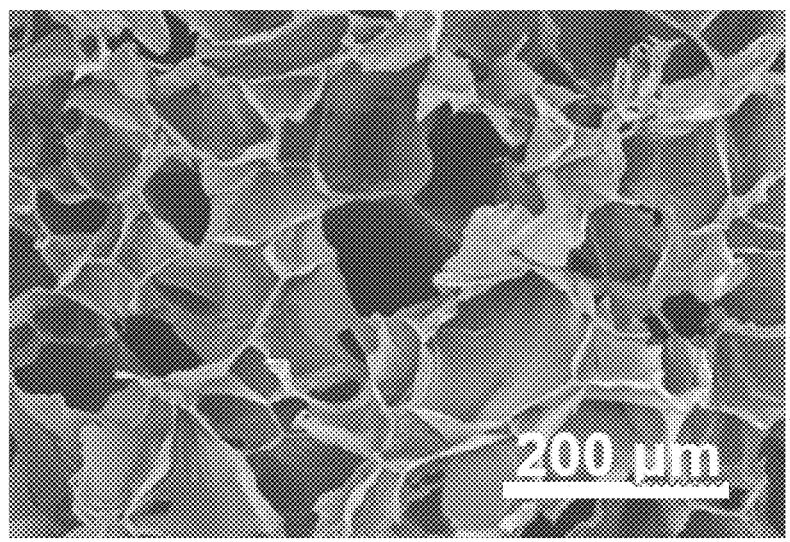
FIG. 9A is a scanning electron microscope (SEM) image of the degradable hydrogel of the present invention, wherein the scale bar is 200 μm.
Figure 9B:
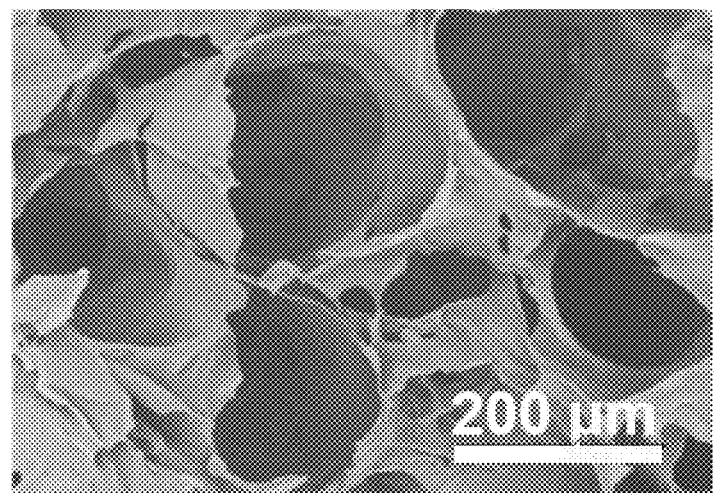
FIG. 9B is a scanning electron microscope image of the cryogel of the present invention, wherein the scale bar is 200 μm.

Scanning Electron Microscope (SEM) Analysis of Degradable Hydrogel and Cryogel and Moisture Absorption Test of Cryogel In this example, the scanning electron microscope (SEM) was used to analyze the pore structure of the degradable hydrogel and cryogel. The results are shown in FIGS. 9A and 9B. As can be seen from FIG. 9A, the degradable hydrogel does not have a structure in which large pores are clearly connected like the cryogel, and the pore size is smaller. As can be seen from FIG. 9B, the characteristics of the cryogel are its large pore connectivity characteristics (the pore wall itself is tightly cross-linked to form a certain supporting force, and the capillary phenomenon can be propped back to its original shape after absorbing water into the colloid), and the pore size is about 200 μm, which is beneficial for the transfer of nutrients and metabolites in cell culture.

Figure 9C:
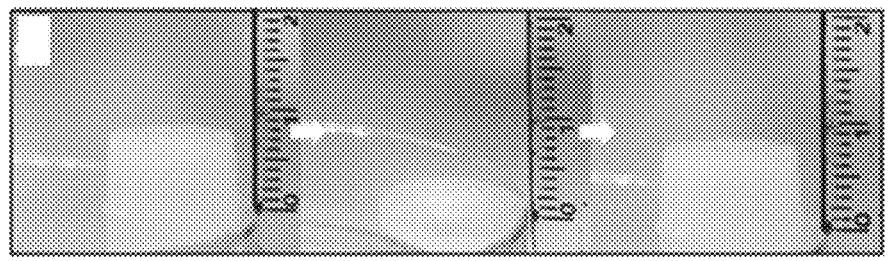
FIG. 9C is a water absorption test diagram of the cryogel of the present invention.

In addition, the moisture absorption test of the cryogel of the present invention was performed. As shown in FIG. 9C, the cryogel was crushed (1 mm of height). At this time, the water in the cryogel was squeezed out and the cryogel can recover its original volume (8 mm of height) after absorbing moisture. The compression rate is 87.5% close to the porosity in Table 3. In addition, the swelling ratio, porosity and compression modulus of the cryogel of the present invention were measured by dynamic mechanical analysis (DMA) (Q-800, TA Instruments) (measured at a deformation rate of 0.1% and a frequency of 1 Hz at 37° C.). The result is shown in Table 3.

TABLE 3

| Swelling ratio (%) | Porosity (%) | Compression modulus (kPa) |
| --- | --- | --- |
| 2730 ± 400 | 86.5 ± 1.6 | 5.8 ± 0.5 |

As can be seen from Table 3, the mechanical strength of the cryogel is about 5.8 kPa, the cryogel has excellent water absorption (the cryogel can absorb about 27 times of water than the original weight), and the colloid would not be destroyed under external force, compressed to the original small volume (at this time the water is squeezed out). In addition, adding water can restore the original shape within a few seconds (this is almost the same as the swelling after three days), which is closely related to its internal structure, and the porosity of the cryogel was measured as high as 86.5%. Therefore, the cryogel of the present invention can immediately absorb moisture.

Example 10

Analysis of Shape Memory and Injectable Properties of Cryogel

Figure 10A:
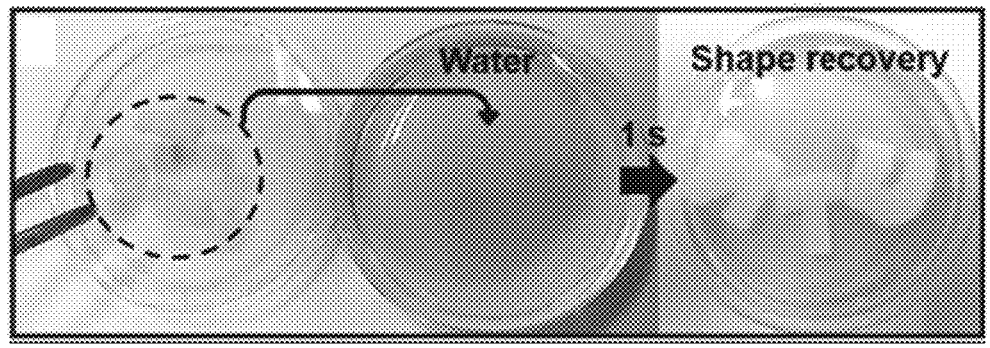
FIG. 10A is a schematic diagram showing the shape memory properties of the cryogel of the present invention.

In this example, the cryogel compresses its volume when it loses water (i.e., dried cryogel), and when placed in water (i.e., wet cryogel), it immediately absorbs water and restores its original shape, as shown in FIG. 10A. This proves that the cryogel of the present invention has shape memory properties.

Figure 10B:
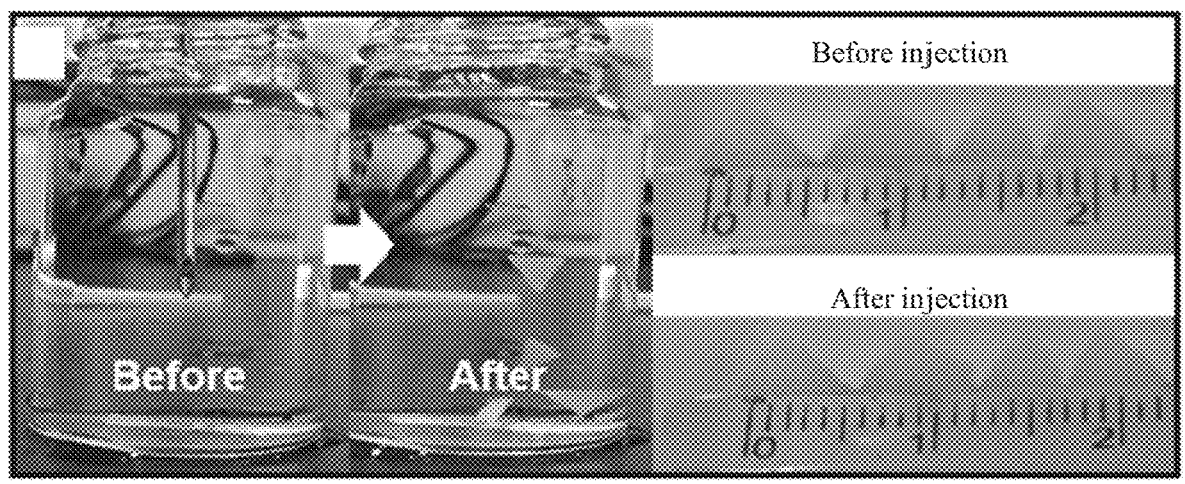
FIG. 10B is a schematic diagram showing the injectable properties of the cryogel of the present invention.

In addition, FIG. 10B is a schematic diagram showing the injectable properties of the cryogel of the present invention. As can be seen from FIG. 10B, the cryogel of the present invention (4 mm long and 1 mm thick) can be injected using an 18G needle (838 μm), and the volume can be reduced through the needle during injection. After injection, it encounters water and returns to the original shape without deformation. Therefore, the cryogel of the present invention has an injectable property, and the advantage is that the biomedical material can be directly injected into the body for application, without the need of a surgical operation, to avoid the pain and repair time caused by surgery.

Example 11

Cytotoxicity Analysis of Crosslinking Agent

Figure 11:
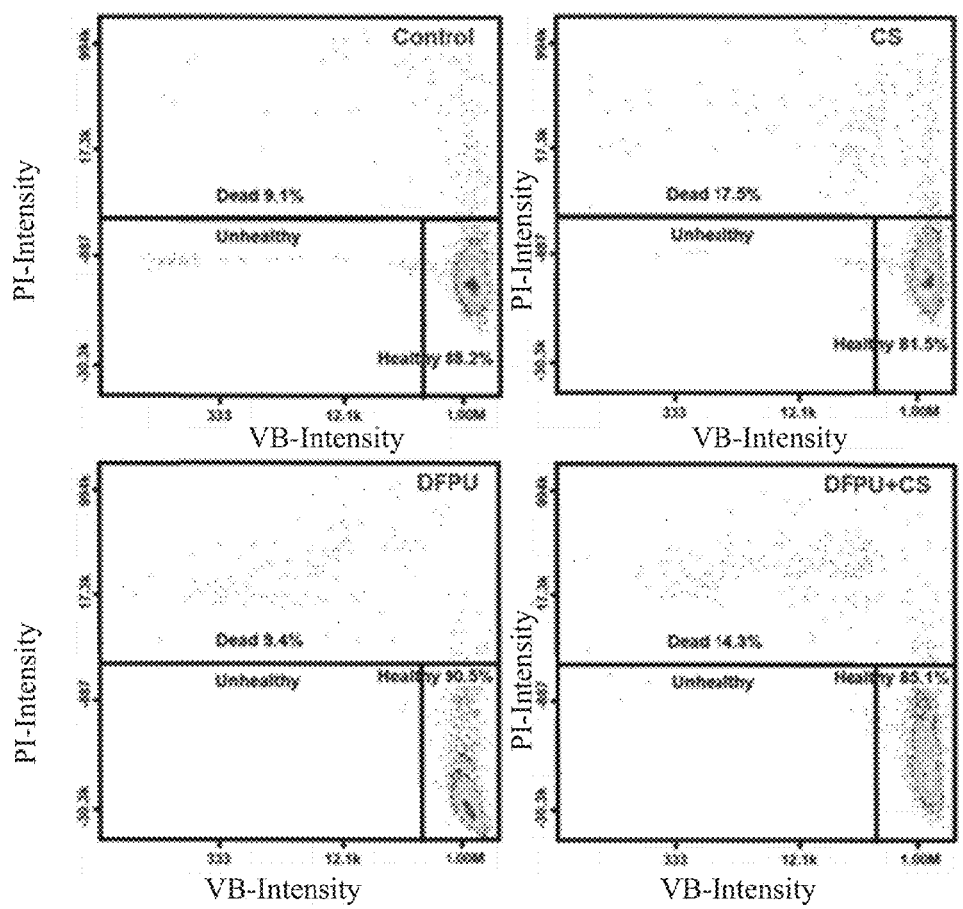
FIG. 11 is a data diagram showing the cytotoxicity analysis of the control group (i.e., cell culture medium), CS, the crosslinking agent, and CS plus the crosslinking agent, wherein control represents the control group; CS represents glycol chitosan; DFPU represents the crosslinking agent.

In this example, the cell survival rate was used to test whether the crosslinking agent of the present invention has cytotoxicity, and the cell survival rate of neural stem cells (NSC) coated in each analysis sample was determined by the VB-48™ reagent. The analysis operation procedure is as follows: the dye was added to the cell-containing material and optical analysis was performed with an analytical instrument, wherein green is acridine orange (AO) staining live cells, red is propidium iodide (PI) staining dead cells, and blue is the VB-48™ reagent, an enzyme that stains mitochondria, wherein more enzymes represent cells have stronger activity. The result is shown in FIG. 11. FIG. 11 is a data diagram showing the cytotoxicity analysis of the control group (i.e., cell culture medium), CS, the crosslinking agent, and CS with the crosslinking agent. It can be seen from FIG. 11 that the cell survival rate of the control group is 88.2%, while the cell survival rates of CS, the crosslinking agent, and CS with the crosslinking agent are 81.5%, 90.5%, and 85.1%, respectively. None of the materials used from the hydrogel has obvious cytotoxicity. The results of this example show that the crosslinking agent of the present invention has no significant cytotoxicity.

Example 12

In Vitro Degradation Test of Cryogel and Degradable Hydrogel

Figure 12:
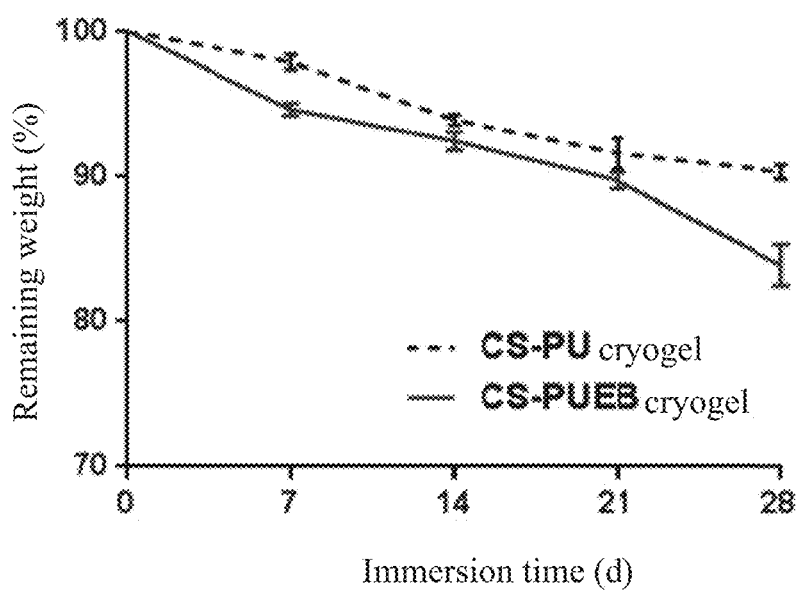
FIG. 12 is a data diagram showing the in vitro degradation test of the cryogel of the present invention.

The crosslinking agent of the present invention is made by modifying PU, in the prior art the degradation rate of PU can be adjusted by adjusting the soft segment of PU. For the same reason, the degradation rate of the crosslinking agent of the present invention can also be adjusted by adjusting the soft segment, and the degradation rate of the prepared degradable hydrogel and cryogel can also be controlled. Therefore, the 28-day in vitro degradation and comparison between the degradable hydrogel (or cryogel) containing CS-PU and the degradable hydrogel (or cryogel) containing CS-PUEB were performed. As shown in FIG. 12, the results show that the degradable hydrogel (or cryogel) containing CS-PUEB has a faster degradation rate.

Example 13

Subcutaneous Experiment of Rat with Cryogel

Figure 13A:
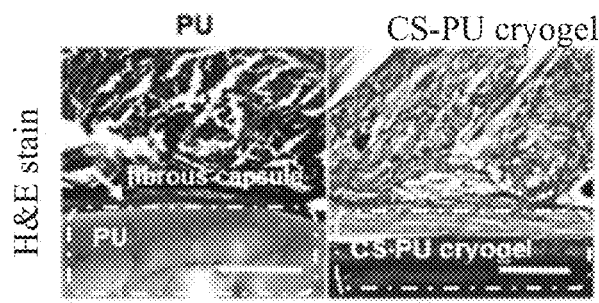
FIG. 13A is a hematoxylin-eosin staining diagram showing a rat subcutaneous experiment regarding the cryogel of the present invention.
Figure 13B:
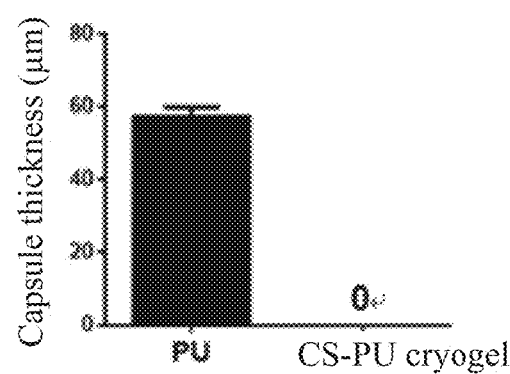
FIG. 13B is a data diagram showing the subcutaneous experiment regarding the cryogel of the present invention.
Figure 13C:
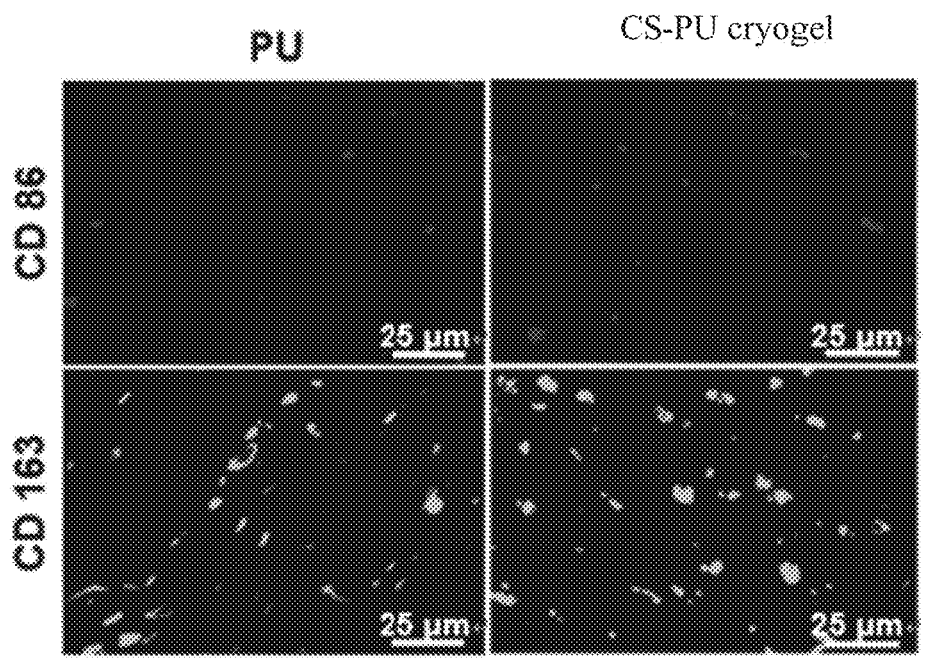
FIG. 13C is an immunofluorescence staining diagram showing the subcutaneous experiment regarding the cryogel of the present invention.
Figure 13D:
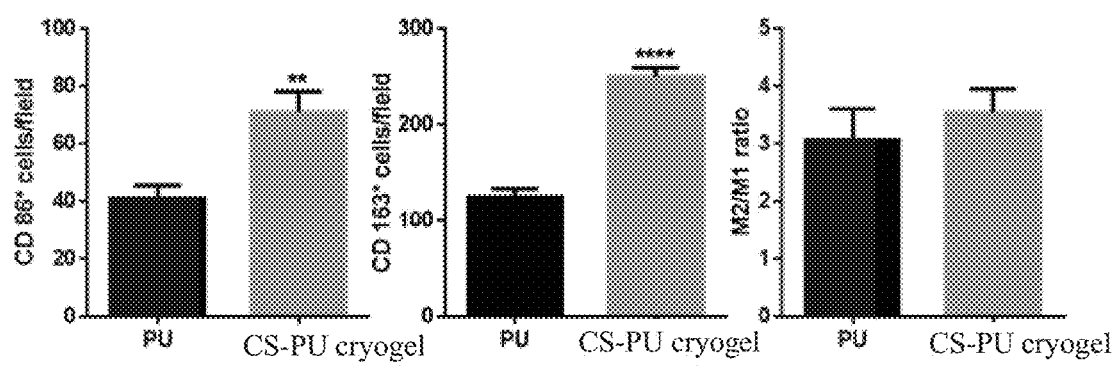
FIG. 13D is a data diagram showing a rat subcutaneous experiment regarding the cryogel of the present invention, wherein  indicates p<0.01; ** indicates p<0.0001.

PU was used as a control group, CS-PU containing cryogel was used as an experimental group, and they were implanted subcutaneously in rats for 14 days. Hematoxylin and eosin stain (H & E stain) was used to observe the foreign material reaction. It can be seen from FIGS. 13A and 13B that PU forms a capsule, but the cryogel of the experimental group does not. The material is covered with immune cells on and around it, which is a slight inflammatory reaction (FIG. 13A). In addition, immunofluorescence staining was performed to confirm the type of immune cells. Antibody CD86 was used to stain M1 macrophages representing inflammation, and antibody CD163 was used to stain M2 macrophages representing repair. As a result, it was found that the repaired M2 macrophages were more than three times that of the M1 macrophages representing inflammation (FIGS. 13C and 13D). This means that although there is inflammation, it is already in the direction of repair at 14th day and has potential as a biomedical material.

Example 14

Shape Memory Performance of Cryogels 14.1 Synthesis of Water-Based Difunctional Polyurethane Crosslinker Three kinds of water-based difunctional polyurethane crosslinkers were synthesized according to previous literature. The first crosslinker with the formula reported previously was synthesized and abbreviated as DFPU1 (T. W. Lin, S. h. Hsu, Self-healing hydrogels and cryogels from biodegradable polyurethane nanoparticle crosslinked chitosan, Advanced Science (2019) 1901388). Two new crosslinkers, abbreviated as DFPU2 and DFPU3, were synthesized from different oligodiols. Design of the new crosslinkers was based on the introduction of a second oligodiol in the soft segment, i.e. poly(L-lactide) diol, which is crystalline and may lead to shape memory effect. During the synthesis of DFPU1, the oligodiol was polycaprolactone diol (PCL diol, Mn≈2000 Da, Sigma-Aldriche). During the synthesis of DFPU2 and DFPU3, the oligodiols contained PCL diol and poly(L-lactide) diol (PLLA diol, Mn≈2000 Da, Purac, Netherlands) in 8:2 and 6:4 mass ratio, respectively. For chemical synthesis, 10 g of oligodiol(s) and 3 g of isophorone diisocyanate (IPDI, Acros) in a glass flask reacted for 3 h with catalyst $Sn(Oct)_2$ at a nitrogen atmosphere of 75° C. 0.6699 g of 2,2-bis(hydroxymethyl) propionic acid (DMPA) and 4.5 g of methyl ethyl ketone (MEK) were put into flask under reflux and reacted for 1 h. Afterwards, 0.505 g of triethylamine (TEA, JT Baker) was added to neutralize carboxylic acid groups at 50° C. and reacted for 30 min. Subsequently, deionized water (DI water) and 0.21 g of ethylenediamine (EDA, Wako) were put in a flask with strong mechanical stirring for 1 h to form nanoparticle polyurethane dispersion. 0.5075 g of glyoxal was added and reacted for 30 min to form difunctional polyurethane crosslinker. The stoichiometric ratio of oligodiol(s)/IPDI/DMPA/EDA/glyoxal was 1:2.7:1:0.7:0.7.

14.2 Synthesis and Characterization of N-Carboxyethyl Chitosan (CEC)

CEC was synthesized by following a previous literature (Y. J. Lin, W. T. Chuang, S. h. Hsu, Gelation mechanism and structural dynamics of chitosan self-healing hydrogels by in situ SAXS and coherent X-ray scattering, ACS Macro Letters 8(11) (2019) 1449-1455). For synthesis, chitosan (Mw=400000 Da, degree of deacetylation 85%, Fluka), DI water, and acrylic acid were put into the flask and reacted at 50° C. for 48 h. The molar ratio of the amine group and carboxyl group was 0.00020:1. The pH value of the CEC solution was adjusted to 11 with 1 N NaOH and dialyzed (12000-14000 MWCO) to remove unreacted substances or small molecules. Lastly, CEC powder was obtained by freeze-drying to remove water and stored at −20° C. The degree of substitution of the CEC prepared by this protocol was approximate 20%. CEC powder was dissolved in d-form acetate acid/$D_2O$ for preparing the NMR sample. The 1H NMR spectrum was detected using a high-resolution spectrometer (Bruker, 500 MHz).

14.3 Preparation of Films and Cryogels

Solid films were prepared by pouring the dispersion of crosslinker on a Teflon dish and removing the residual solvent. To make difunctional polyurethane crosslinked chitosan cryogels (abbreviated as chitosan-PU cryogels), CEC or ethylene glycol chitosan (GC, Mw=400000 Da, degree of deacetylation 78.2%, Sigma) was mixed with DFPU1 or DFPU2 dispersion uniformly, and frozen in a refrigerator at −17° C. for 48 h, and the mixtures were left at room temperature for 1 h to form cryogels. The cryogel obtained from the mixture of GC and DFPU1 was abbreviated as GC-PU1, and that from the mixture of GC and DFPU2 was abbreviated as GC-PU2. The cryogel obtained from the mixture of CEC and DFPU2 was abbreviated as CEC-PU2.

14.4 Evaluation of Shape Memory Properties of Films and Cryogels

The macroscopic shape-memory behaviors of films and cryogels were evaluated by the U-bend test. The film was cut to a length of 10 mm, a width of 4 mm and a thickness of 2 mm. First of all, the film was placed in an oven at 50° C. for 5 min, and then deformed into U-shape. Then, the film was placed at −17° C. for 5 min and held at 25° C. for 1 min to measure the fixed angle ($\theta_A$). Finally, the film was placed at 50° C. for 5 min to measure the recovery angle ($\theta_B$) after holding at 25° C. for 1 min. The procedure for shape memory evaluation of cryogels was the same as that of films. Moreover, the recovery of the cryogel in 4° C. and 50° C. water was also evaluated. The dried cryogel was fixed in a U-shape and kneaded into a mass. The dried cryogel was then immersed in 4° C. water for 5 minutes to get the first shape recovery angle ($\theta_{B,1}$), and soaked the hydrated cryogel in 50° C. water for 5 minutes to obtain the second shape recovery angle ($\theta_{B,2}$). The fixity ratio and recovery ratio were defined as follows:

$$\text{Shape fixity ratio (\%)} = \frac{\theta_A}{180} \times 100 \quad (1)$$

$$\text{Shape recovery ratio (\%)} = \frac{180 - (\theta_B, \theta_{B,1} \text{ or } \theta_{B,2})}{180} \times 100 \quad (2)$$

The microstructural changes during the shape memory process were evaluated by the in-situ wide-angle X-ray scattering (WAXS) experiments at the beamLine 23A of the National Synchrotron Radiation Research Center (NSRRC) at Hsinchu, Taiwan. Three different modes were obtained in the initial, fixed, and recovered states. The initial state was the state before deformation. The switching temperature stretching machine was equipped to stretch the film to 50% strain (or compress the chitosan-PU cryogel to 50% strain) at a temperature of 50° C. and then cool to a temperature of −17° C. to adapt to the requirements of the temporary shape (fixed state). Finally, the temperature was raised to 50° C. (recovery state). The wavelength of the radiation, photon energy, and the range of the scattering vector were 0.154 nm, 10 keV, and 0.002 to 0.2 Å$^{-1}$, respectively.

14.5 Injectability of Shape Memory Cryogel

The dried GC-PU2 cryogel (10 mm×10 mm×1 mm) was fixed into a rod shape by the previously mentioned shape memory process. The rod-shaped cryogel was put into a syringe filled with 4° C. water, injected it through a 16G needle (internal diameter 1.194 mm) into a container filled with 50° C. water, and observed the recovery behavior of the cryogel. The results are shown in FIGS. 14 and 15.

Figure 14:
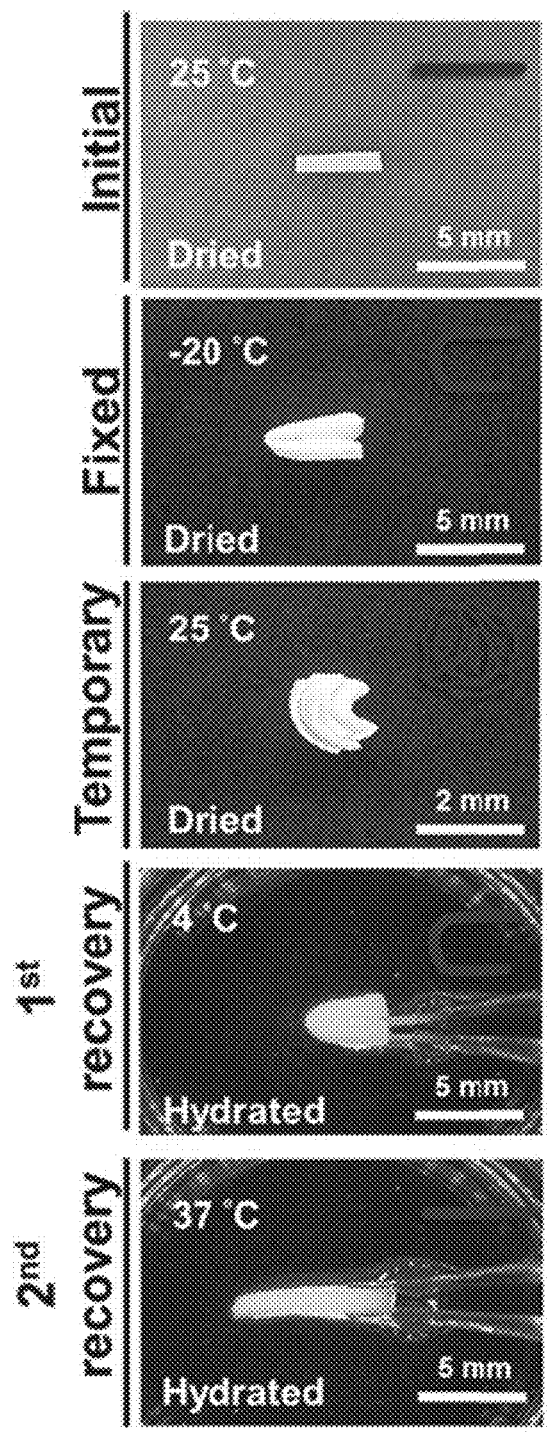
FIG. 14 shows shape memory behavior of GC-PU2 cryogel at 4° C. and 37° C. water. The actual performance of GC-PU2 cryogel was bent from the initial shape (long strip) to the fixed shape (U shape) at 50° C. After being crumpled up, GC-PU2 could recover to U-shape correctly at 4° C. water, and recovery to long strip exactly at 37° C. water.

FIG. 14 shows shape memory behavior of GC-PU2 cryogel at 4° C. and 37° C. water. The actual performance of GC-PU2 cryogel was bent from the initial shape (long strip) to the fixed shape (U shape) at 50° C. After being crumpled up, GC-PU2 could recover to U-shape correctly at 4° C. water, and recovery to long strip exactly at 37° C. water.

Figure 15:
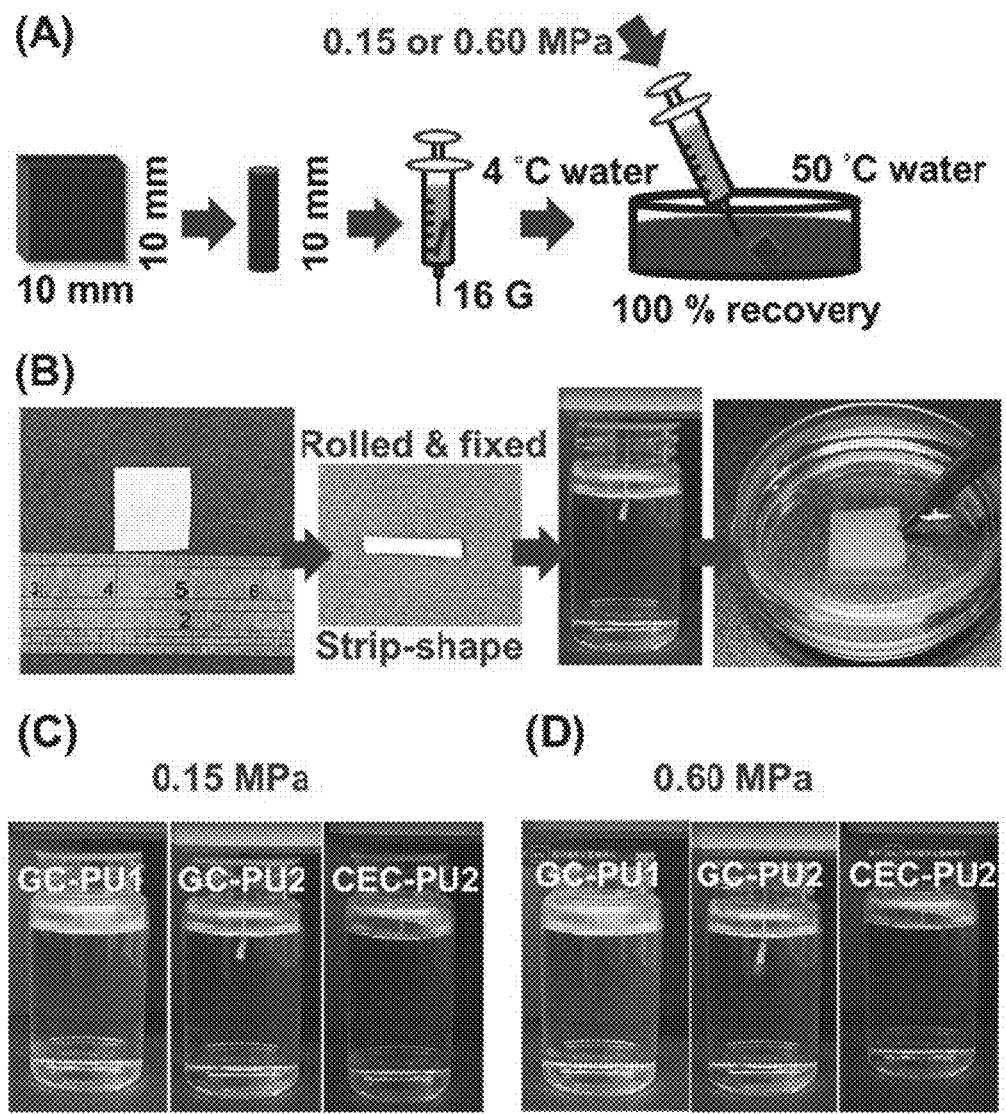
FIG. 15 shows injectability of the shape memory cryogel. (A) The schematic diagram depicting the injection of GC-PU2 cryogel. (B) The shape memory cryogel (length 10 mm×width 10 mm×thickness 1 mm) was curled from the initial sheet-like shape into the rod-like shape at 50° C. and fixed at −17° C. The cryogel remained the rod shape in a syringe filled with 4° C. water. Finally, the cryogel was injected through a 16G (inner diameter 1.194 mm) needle into 37° C. water to restore the original shape (sheet) without deformation. (C) GC-PU2 cryogel could be extruded by the pressure of 0.15 MPa. (D) GC-PU1 and CEC-PU2 also could not be extruded by the maximum pressure of 0.60 MPa.

FIG. 15 shows injectability of the shape memory cryogel. (A) The schematic diagram depicting the injection of GC-PU2 cryogel. (B) The shape memory cryogel (length 10 mm×width 10 mm×thickness 1 mm) was curled from the initial sheet-like shape into the rod-like shape at 50° C. and fixed at −17° C. The cryogel remained the rod shape in a syringe filled with 4° C. water. Finally, the cryogel was injected through a 16G (inner diameter 1.194 mm) needle into 37° C. water to restore the original shape (sheet) without deformation. (C) GC-PU2 cryogel could be extruded by the pressure of 0.15 MPa. (D) GC-PU1 and CEC-PU2 also could not be extruded by the maximum pressure of 0.60 MPa.

Figure 16:
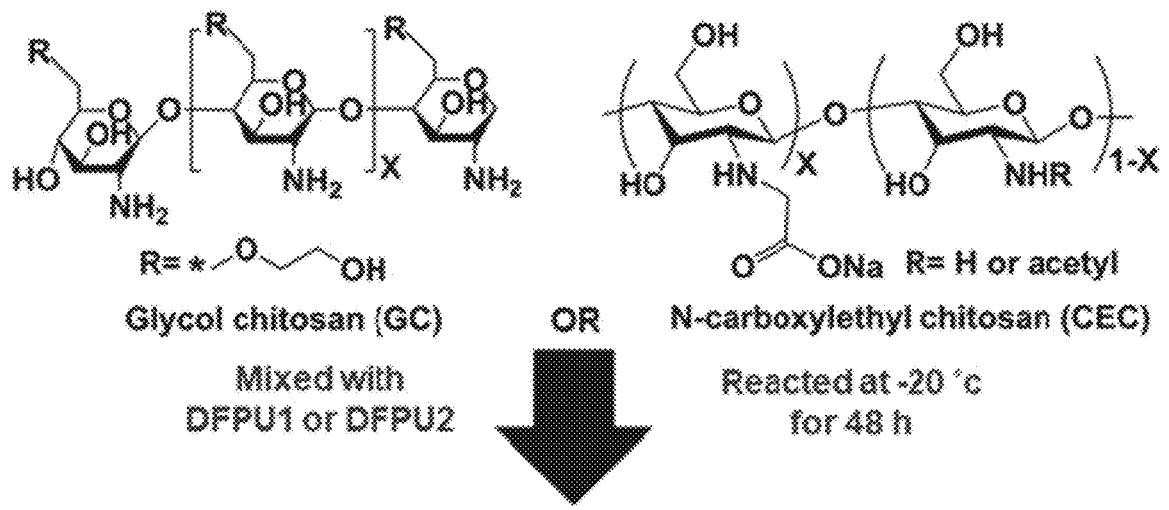
FIG. 16 shows schematic representation of the mixing and freezing process to form chitosan-polyurethane cryogels from different chitosan main chain and polyurethane crosslinker; and formation of various chitosan-PU cryogels by crosslinking. The picture on the right shows the appearance of GC-PU2 cryogel.
Figure 16:
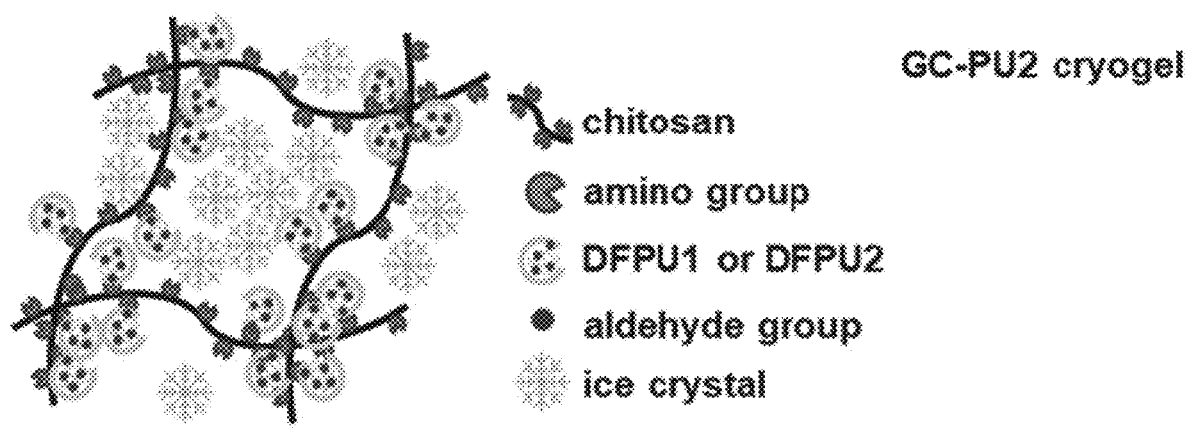

14.6 Shape Memory and Thermal Properties of New Difunctional Polyurethane Crosslinkers and Various Cryogels A schematic diagram of the preparation of chitosan-PU cryogels is shown in FIG. 16. Chitosan-PU cryogels were obtained after melting the ice crystals and air drying. The contents of shape memory chitosan-PU cryogels were first optimized by U-bend tests in air and results are summarized in Table S1. It was found that chitosan in 2 wt % and DFPU2 in 2 wt % led to better shape recovery ratio and shape fixation ratio. Therefore, in the main study, the cryogels were prepared with 2 wt % chitosan and 2 wt % polyurethane crosslinker. The three cryogels in the main study include GC-PU1 cryogel prepared from 2 wt % GC and 2 wt % DFPU1, GC-PU2 cryogel from 2 wt % GC and 2 wt % DFPU2, and CEC-PU2 cryogel from 2 wt % CEC and 2 wt % DFPU2 (Table 3).

TABLE 3

| Sample | Shape memory performance (in air) | | Crystallinity | | |
|---|---|---|---|---|---|
| | Shape fixity (%) | Shape recovery (%) | Total (%) | From PLLA (%) | From PCL (%) |
| DFPU1 | 85.4 ± 1.1 | 80.1 ± 6.6 | 7.63 | 0 | 7.63 |
| DFPU2 | 97.6 ± 1.5 | 80.3 ± 3.1 | 4.52 | 0.21 | 4.31 |
| GC-PU1 | 91.2 ± 2.5 | 41.1 ± 1.6 | 4.90 | 0 | 4.90 |
| GC-PU2 | 99.2 ± 0.8 | 67.2 ± 1.8 | 3.41 | negligible | 3.41 |
| CEC-PU2 | 86.1 ± 1.1 | 51.2 ± 0.5 | 3.51 | negligible | 3.51 |

*Glycol chitosan was abbreviated as GC, and N-carboxylethyl chitosan was abbreviated as CEC.

Figure 17A:
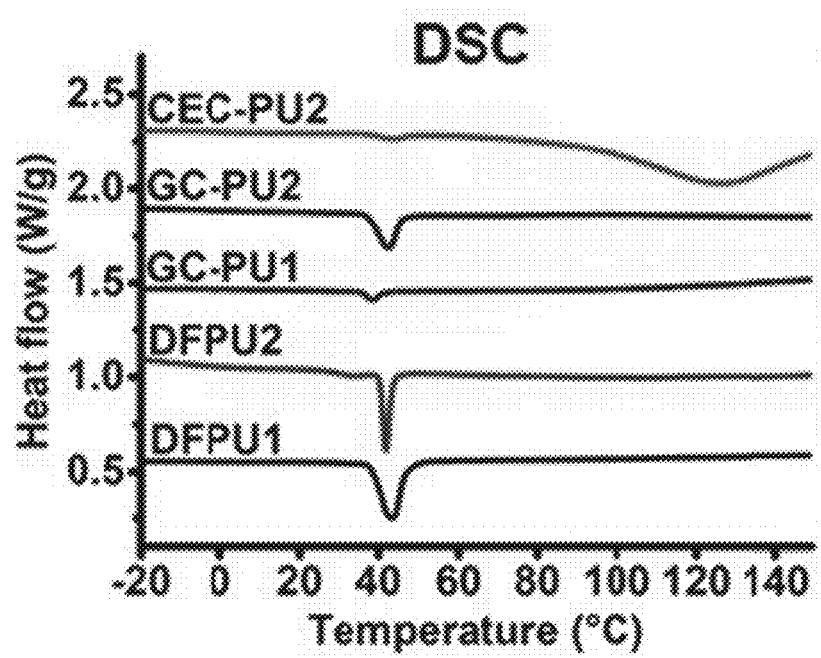
FIGS. 17A-17D show characterization of DFPU and CS-PU cryogels by DSC, XRD and WAXS. (A) The DSC curves and (B) the XRD profiles of DFPU films and various chitosan-PU cryogels. (C) One-dimensional in-situ WAXS patterns collected during the shape memory testing (25° C./50° C./−20° C./50° C.) of DFPU2 and GC-PU2. (D) One-dimensional in-situ WAXS patterns collected during the shape memory testing (25° C./50° C./−20° C./50° C.) of DFPU1, GC-PU1, and CEC-PU2.

The DSC curves of DFPU1, DFPU2 and various chitosan-PU cryogels are demonstrated in FIG. 17A. The endothermic peak ranging from 38-52° was ascribed to the crystallinity of PCL. The $T_m$ of DFPU1 and DFPU2 were 43.6° C. and 42.1° C., respectively. The presence of PLLA slightly reduced the $T_m$ in DFPU2. Moreover, GC-PU2 (42.4° C.) and CEC-PU2 (43.5° C.) cryogels had higher $T_m$ than GC-PU1 (38.8° C.) cryogel. Besides, CEC-PU2 cryogel had a broad endothermic peak near 125.9° C., which was associated with the strong intermolecular and/or intramolecular hydrogen bonding caused by the hydrophilic —OH group of CEC.

Figure 17B:
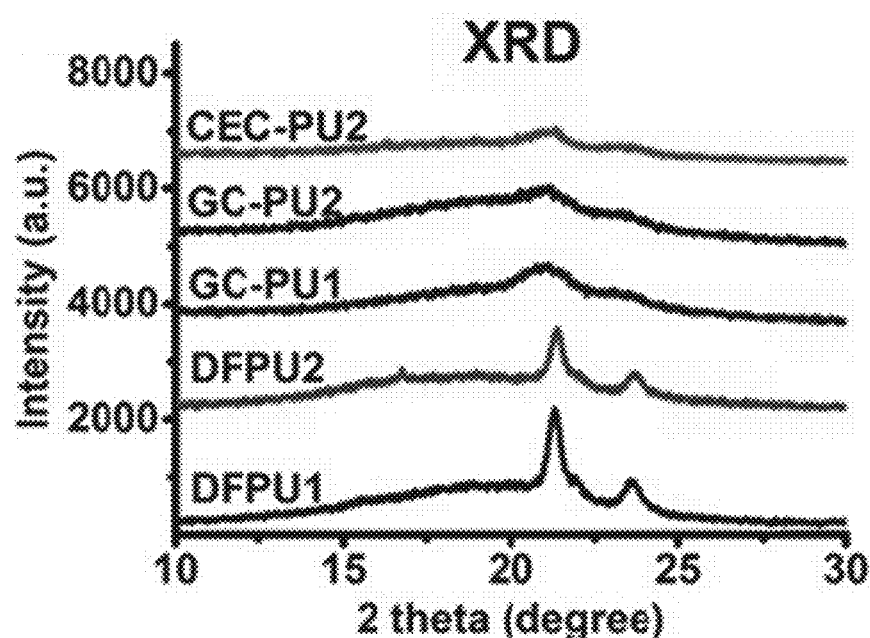
Figure 17C:
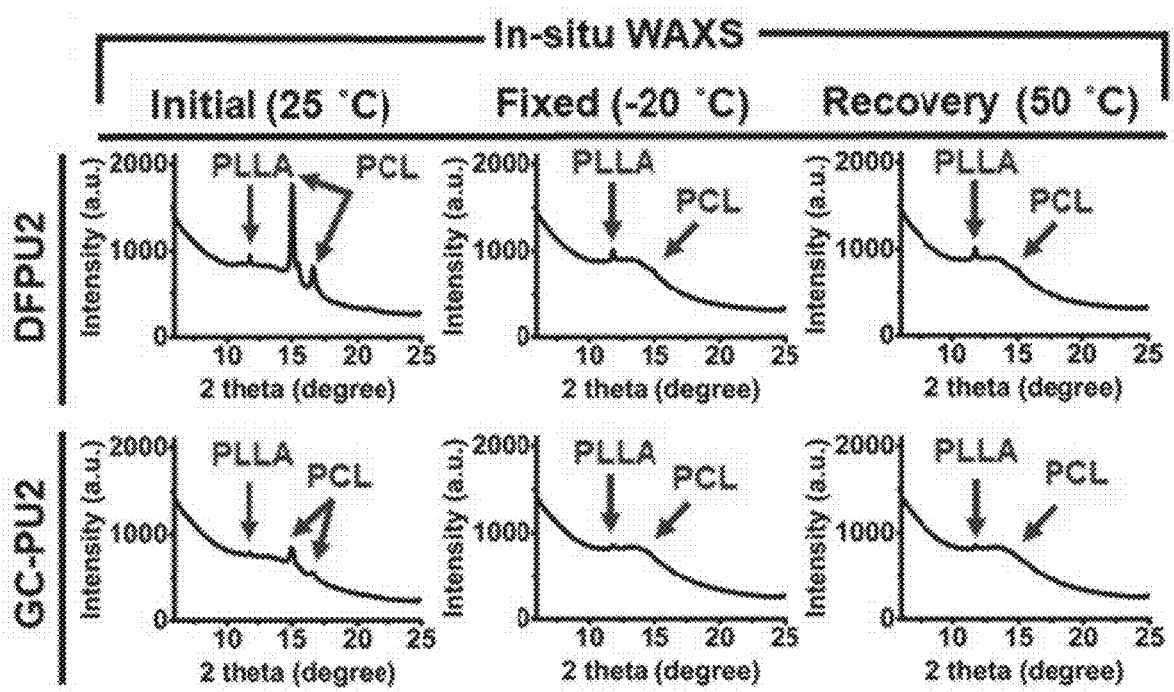
Figure 17D:
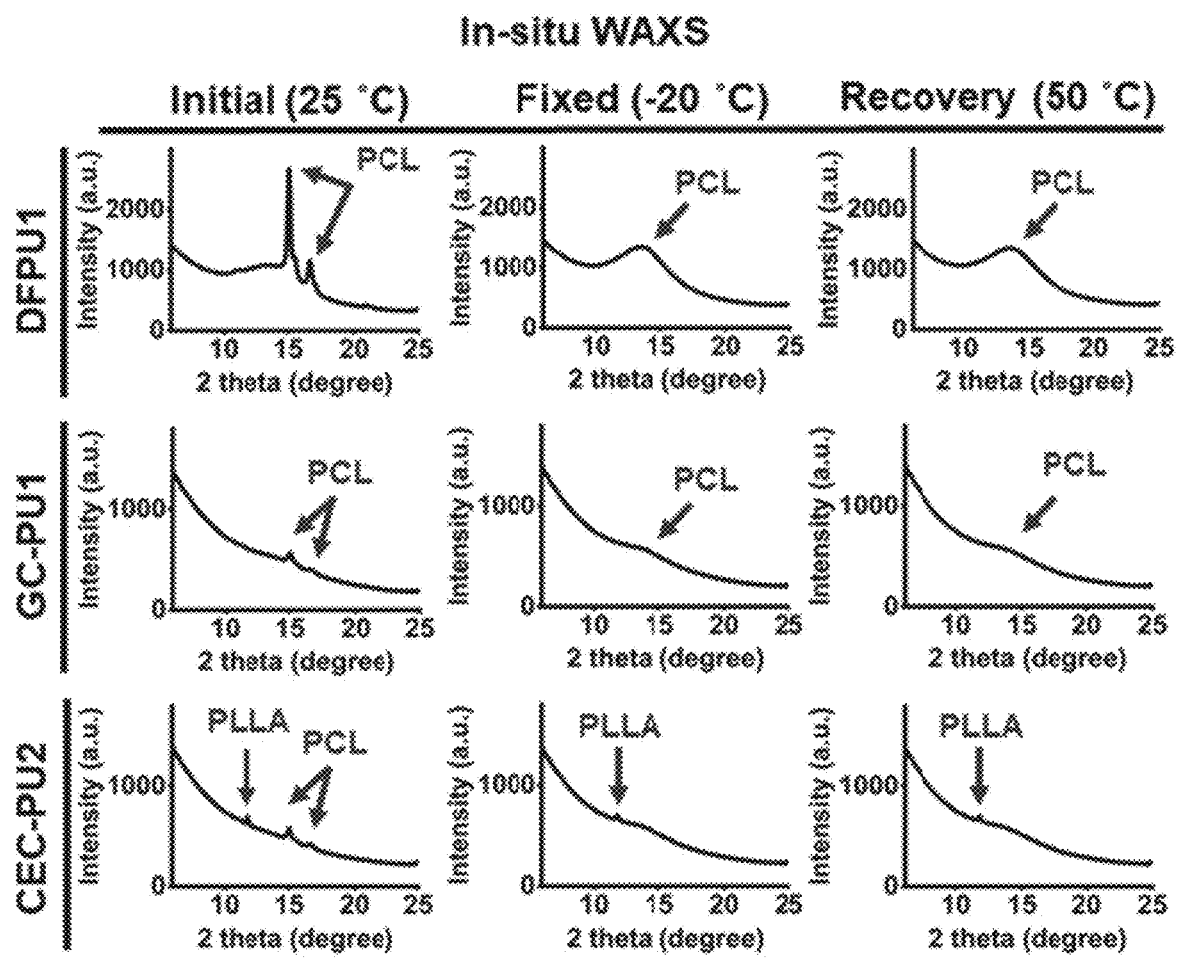

The XRD patterns of DFPU1, DFPU2, and various cryogels are shown in FIG. 17B. The diffraction peak at 16.8° was attributed to PLLA. Moreover, the diffraction peaks around 21.3° and 23.5° were attributed to PCL. The crystallinity of DFPU1, DFPU2, and various cryogels is summarized in Table 3. There were 7.63% crystallinity attributed to PCL in DFPU1. In DFPU2, 4.31% crystallinity was attributed to PCL and 0.21% crystallinity was attributed to PLLA. The crystallinity of PCL was reduced by 2.73% after DFPU1 crosslinked with GC to form cryogel, whereas the crystallinity of PCL in DFPU2 was reduced by 0.9% and 0.8% after DFPU2 crosslinked with GC and CEC to form cryogel, respectively. The one-dimensional in-situ scattering patterns collected during the shape memory process through the combination of WAXS and the tensile tester are demonstrated in FIGS. 17C and 17D. At the initial state, the samples were untreated. In the fixed state, the sample was deformed to 50% strain under 50° C. and cooled to −17° C. to maintain the deformation. In the recovery state, the sample was heated to 50° C. to recover. The DFPU2 film at the initial state showed a PLLA peak at 11.8° and three PCL peaks at 15.1°, 15.5°, and 16.4°. In the fixed state, three PCL peaks declined significantly and only one peak existed at 15.1°, while the PLLA peak remained nearly unchanged. The WAXS pattern in the recovery state was similar to that in the fixed state. The GC-PU2 cryogel prepared from glycol chitosan and DFPU2 displayed a PLLA peak (11.8°) and two PCL peaks (15.1° and 16.4°), which were all smaller than those in the DFPU2 film in the initial state. At the fixed and restored states, the PCL in GC-PU2 revealed a broad amorphous band. Meanwhile, CEC-PU2 cryogel had similar WAXS patterns to GC-PU2 cryogel in the initial state. However, the PCL peaks of CEC-PU2 cryogel disappeared after deformation and recovery. In addition, DFPU1 showed three PCL peaks (15.1°, 15.5°, and 16.4°) in the initial state and produced a broad amorphous band of PCL in the fixed and recovery states. Moreover, the GC-PU1 cryogel only exhibited two PCL peaks (15.1° and 16.4°) which were significantly smaller than those in DFPU1. A rather small PCL broad amorphous band was observed after fixation and recovery of GC-PU1.

Figure 18:
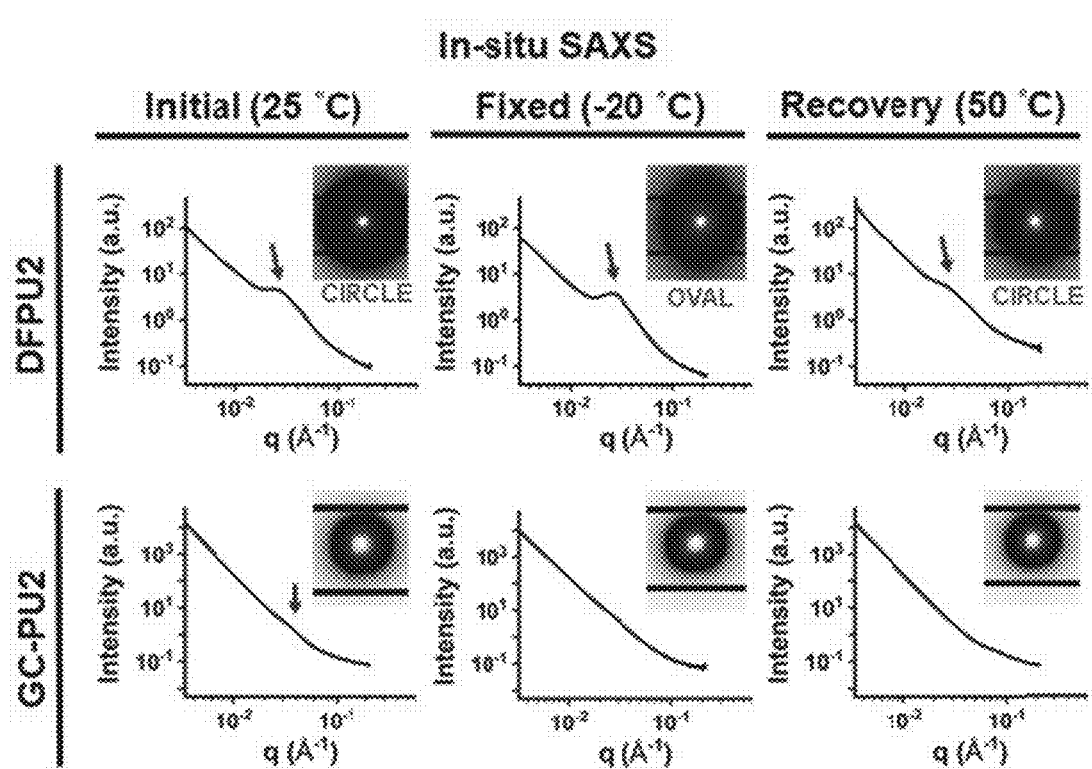
FIG. 18 shows one-dimensional and two-dimensional in-situ SAXS patterns collected during the shape memory testing (25° C./50° C./−20° C./50° C.) of DFPU1, DFPU2, and GC-PU2.
Figure 19:
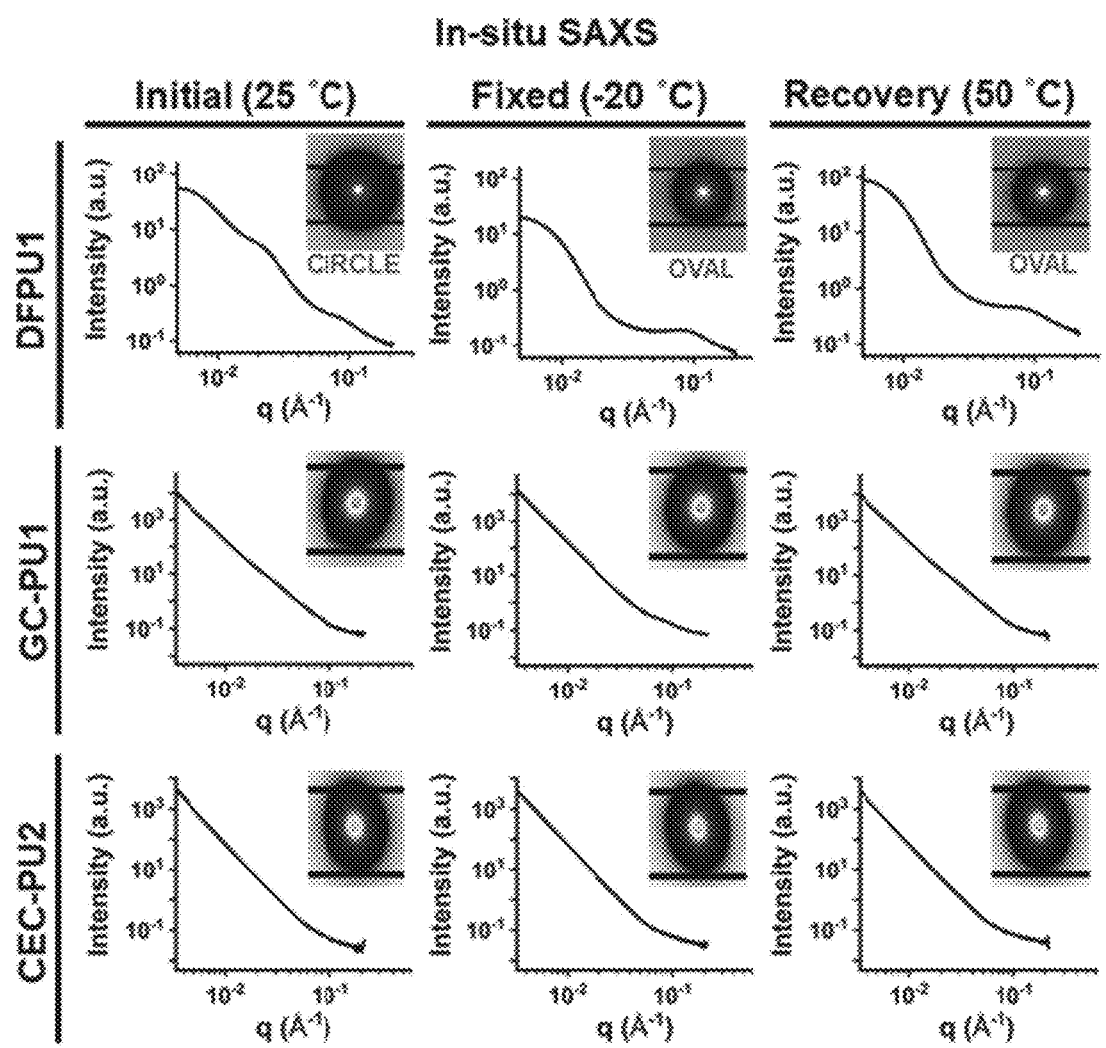
FIG. 19 shows one-dimensional and two-dimensional in-situ SAXS patterns collected during the shape memory testing (25° C./50° C./−20° C./50° C.) of DFPU1, GC-PU1, and CEC-PU2.

The one-dimensional (1D) and two-dimensional (2D) in-situ scattering patterns collected during the above shape memory process through the combination of SAXS and the tensile tester are further demonstrated in FIGS. 18 and 19. The DFPU1 film revealed an asymptotic 1D curve in the initial state. In the fixed state, the q value showed a broad peak at about $10^{-1}$ Å$^{-1}$ and the intensity of the broad peak decreased slightly after the shape was restored. The corresponding 2D pattern of the DFPU1 film showed that the red area ranged from a circle (initial state) to an ellipse (fixed state), and returned to an ellipse in the recovery state. Comparing the 1D curve of DFPU2 to that of DFPU1, the initial q value for DFPU2 had a broad peak at about $3 \times 10^{-2}$ Å$^{-1}$. The intensity of the broad peak raised in the fixed state and then quickly dissipated in the recovery state for DFPU2. The 2D patterns of DFPU2 showed a circle in the initial state, an oval in the fixed state, and then partially returned to a circle in the recovery state. The 1D curve and 2D pattern of DFPU2 indicated that the PLLA segment in the structure was closely associated with its shape memory behavior. Despite that GC-PU2 had a similar 2D pattern as that of DFPU2, a slightly broad peak at the q value of about $4 \times 10^{-2}$ Å$^{-1}$ was found at the initial state but could not be observed at the fixed and recovery states in the 1D curve. Meanwhile, GC-PU1 and CEC-PU2 did not demonstrate any peak in 1D curves for the three states. In summary, the slightly broad peak at $4 \times 10^{-2}$ Å$^{-1}$ was closely associated with the shape memory ability of the GC-PU2 cryogel.

Example 15

3D Printing of Cryogels 15.1 Synthesis of Difunctional Polyurethane (DPU) Crosslinkers The water dispersion of difunctional polyurethane (DPU) was synthesized by a water-based process. Oligodiols of four different types were used as the soft segment, including poly(ε-caprolactone) (PCL) diol (Mn=2000 Da, Sigma-Aldrich), poly(ethylene adipate) glycol (PEBA, Mn=2000 Da, Yong Shun Chemical, Taiwan), poly(l-lactide) (PLLA) diol (Mn≈2000 Da), and poly(d,l-lactide) (PDLLA) diol (Mn≈1500 Da). The latter two oligodiols were first produced in the laboratory by the ring-opening polymerization of dilactide (Purace) with 1,3-propanediol (Alfa Aesar, UK) in the presence of catalyst 0.05% stannous octoate (Sn(Oct)2, Alfa Aesar).

Various DPU crosslinkers were synthesized following the previous literature (Lin T-W, Hsu S-h. Self-Healing Hydrogels and Cryogels from Biodegradable Polyurethane Nanoparticle Crosslinked Chitosan. Advanced Science. 2019; n/a:1901388). For each DPU crosslinker, the molar ratios of the oligodiols are listed in Table 4, with the designation DPU1, DPU2, DPU3, and DPU4 for four different DPU crosslinkers. Table 4 shows the compositions and properties of difunctional polyurethanes (DPUs) prepared in the present invention.

TABLE 4

| Sample | Composition (mol %) | | | | Molecular weight | |
| --- | --- | --- | --- | --- | --- | --- |
| | PCL | PDLLA | PEBA | PLLA | $M_w$ (1*10$^4$ Da) | $M_w/M_n$ |
| PU* | 0.8 | 0 | 0 | 0.2 | 7.45 | 1.56 |
| DPU1 | 0.8 | 0.2 | 0 | 0 | 3.31 | 1.52 |
| DPU2 | 1 | 0 | 0 | 0 | 3.41 | 1.45 |
| DPU3 | 0.8 | 0 | 0.2 | 0 | 3.75 | 1.65 |
| DPU4 | 0.8 | 0 | 0 | 0.2 | 4.08 | 1.61 |

PU*: non-functional PU

To synthesize the crosslinker, PCL diol alone or PCL diol in combination with another type of oligodiol (PEBA, PDLLA or PLLA diol) were added in a 250 mL, four-necked flask with mechanical stirring (180 rpm) under a nitrogen environment at 95° C. for 30 min. The hard segment IPDI with the catalyst 0.03% tin(II)2-ethylhexanate (T-9, Alfa Aesar) for 3 h under nitrogen atmosphere at 75° C. DMPA (DMPA, Sigma, USA) and methyl ethyl ketone (MEK, J. T. Baker) were then poured into the flask and reacted at the same temperature and under nitrogen atmosphere for 1 h. The temperature of the entire system was lowered to 45° C. and then triethylamine (TEA, RDH) was added and reacted for 30 min. Deionized water was added with stirring at 1200 rpm to generate the aqueous dispersion of PU NPs. EDA (EDA, Wako) was added with continuous stirring for 1 h before glyoxal (Alfa Aesar) was added with continuous stirring for 1 h. MEK and TEA were removed from the system by reduced pressure after the reaction was completed. The molar ratio of the reactants IPDI/oligodiols/DMPA/TEA/EDA/glyoxal was 2.7:1:1:1:0.7:0.7.

The DPU nanoparticles (DPU NPs) had a solid content about 30 wt % in aqueous dispersion. The size and zeta potential of the DPU NPs in dispersion were determined by the submicron particle analyzer (Delsa™ Nano, Beckman Coulter, USA) involving principles of dynamic light scattering and electrophoretic light scattering after the concentration of the DPU dispersion was diluted to 3000 ppm. The morphology of the DPU NPs was observed by a transmission electron microscope (TEM; TEM-1200 EX II, JEOL, Japan). The TEM samples were prepared by diluting the PU dispersion to 3000 ppm and mixing with an equal volume of osmium tetroxide for 30 min. The sample was fixed on the copper grid for 30 min and dried at room temperature for 24 h before examination. DPU films were cast from the DPU dispersion on Teflon plates and dried at room temperature for 3 d. The molecular weight ($M_w$) of DPUs was determined with the gel permeation chromatography (GPC, JASCO, Japan). The sample for GPC was prepared by dissolving 3 mg of the PU film in 100 μl of N, N-dimethylacetamide (DMAc, Tedia). The functional groups of PU were identified by the attenuated total reflectance-Fourier transform infrared spectroscopy (ATR-FTIR). The film sample was scanned with a resolution of 0.5 $cm^{-1}$ in the wavenumber of 4000-750 $cm^{-1}$.

15.2 Preparation and Characterization of Glycol Chitosan (CS)/DPU Self-Healing Hydrogel The water-soluble glycol chitosan (CS, Sigma) was prepared with deionized water (1.5-6 wt %). Various DPU crosslinkers were prepared in deionized water (3-9 wt %). CS solution was blended with DPU dispersion to obtain CSDPU self-healing hydrogels at 25° C.

The rheological properties of CSDPU self-healing hydrogel was examined by a rheometer (Rheometric RS5, TA) at 25° C. The storage modulus and loss modulus (G' and G") were determined against time at a constant frequency of 1 Hz (6.28 rad/s) and 1% strain. After that, the frequency sweep was obtained at a constant strain of 1% in the angular frequency range (1-100 rad/s). The dynamic strain sweep was evaluated at a frequency of 1 Hz from 0.1% to 700% strain. The shear thinning property was analyzed by the steady shear experiment, where the viscosity was measured against the shear rate. For quantitative evaluation of the self-healing process, G' and G" at the constant frequency of 1 Hz were measured by damage-healing cycles at the high strain (500%) for damage and at the low strain (1%) for healing.

15.3 Preparation and Characterization CSDPU Cryogel

CS solution was blended with DPU dispersion at 4° C. for 4 h. The mixture was placed at −17° C. for 48 h. The gel was then moved to 25° C. to melt the ice crystal and form the CSDPU cryogel.

The morphologies of the CSDPU cryogel (cross-section) were examined by a scanning electron microscope (SEM, Hitachi TM3000, Japan) operated in 3 kV. CSDPU cryogel was coated with platinum for 80 s as a conductive layer for image observation. The porosity of the CSDPU cryogel was measured by infiltration in water. The percent porosity was calculated by the equation $(W_w-W_d)/pV \times 100\%$, where $W_w$ was the wet weight of CSDPU cryogel after infiltration in water, $W_d$ was the dry weight of CSDPU cryogel before infiltration, p was the density of water, and V was the volume of the CSDPU cryogel.

The water swelling ratio of the cryogel was measured against time at 37° C. The swelling ratio of the cryogel was calculated by the equation $(W_w-W_i)/W_i \times 100$ where $W_i$ was the initial weight of the sample and $W_w$ was the wet weight of the samples at the respective time interval. The dynamic compression modulus of the cryogel was obtained by a dynamic mechanical analyzer (DMA, Q800, TA, USA) operating at 25° C., a constant frequency of 1 Hz, and 0.1% compression strain. The degradation rate of CSDPU cryogel was evaluated in phosphate buffered saline (PBS) under 37° C. Before the experiment, CSDPU was rinsed thoroughly with deionized water and freeze-dried before weighing ($W_i$). Samples were washed with deionized water, freeze-dried, and weighed ($W_f$) after 7, 14, 21, and 28 d. The remaining weight of samples was obtained by the equation $W_f/W_i \times 100\%$.

15.4 Fabrication of CSDPU Cryogel Scaffolds by 3D Printing

In order to make the hydrogel printable, the mixing process was first optimized. The CS solution was blended with DPU under 4° C. for 4 h to form the pre-cryogel. The rheological properties of the pre-cryogel were examined by the rheometer at 4° C. The pre-cryogel was used as the printing materials. Scaffolds were fabricated by a commercial 3D bioprinter (Regenovo Biotechnology, China) using the liquid-frozen deposition manufacturing (LFDM) system. The stacking fibers were extruded with designed contour and paths on a −20° C. platform through a 0.21 mm nozzle under a constant pressure 0.16 MPa and, the extrusion velocity was 6.5 mm/s. The scaffold was frozen at −17° C. for 48 h to form the cryogel scaffolds. Scaffolds were dried for further experiments.

The morphologies of the CSDPU cryogel scaffolds (cross-section) was examined by the SEM, as described in Example 15.3. The porosity, water swelling ratio, dynamic compression modulus, and degradation rate were measured as also described in Example 15.3. To evaluate the injectability of the scaffold, the 3D-printed CSDPU cryogel scaffolds (4*9 mm side length, 2 mm thickness) were squeezed to pass through an 18-gauge needle (838 μm inner diameter).

The degree of chemical crosslinking for the dried DPU1 films, CSDPU gel, CSDPU cryogel, and CSDPU 3D-printed cryogel was estimated by the equilibrium swelling method. The samples were lyophilized for 24 h and weighed ($W_e$). The samples were immersed in MEK for 24 h. They were dried in a vacuum oven at 25° C. until constant weight ($W_d$). The gel fraction (%) for each sample was calculated from the equation $(W_d/W_e) \times 100\%$.

15.5 3D Printing of Cryogel

Figure 20A:
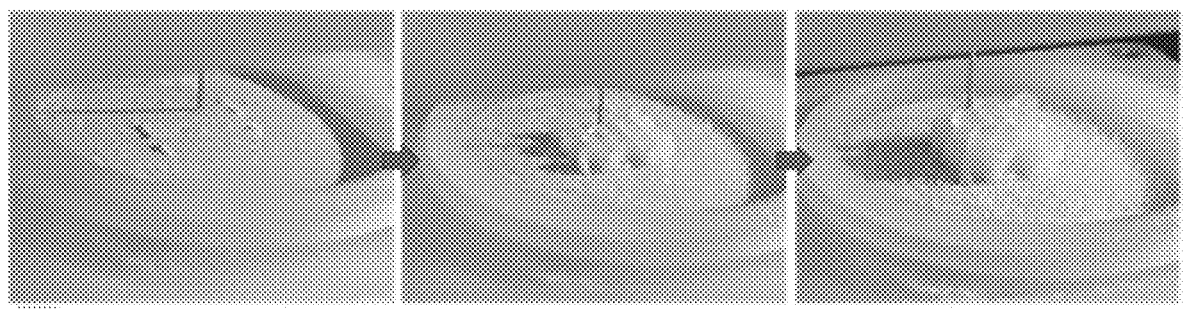
FIGS. 20A-20D show characteristics of 3D-printed CSDPU cryogel (CS 1.5 wt % and DPU 1.5 wt %). (A) The printing process and the 3D-printed CSDPU pre-cryogel. (B) The scaffolds of CSDPU pre-cryogel fabricated prepared by the 3D printer. (C) The SEM image for the microstructure of the CSDPU cryogel scaffold and for the porous structure of the stacking fibers. (D) The compressed cryogel could recover to its initial shape in water.
Figure 20B:
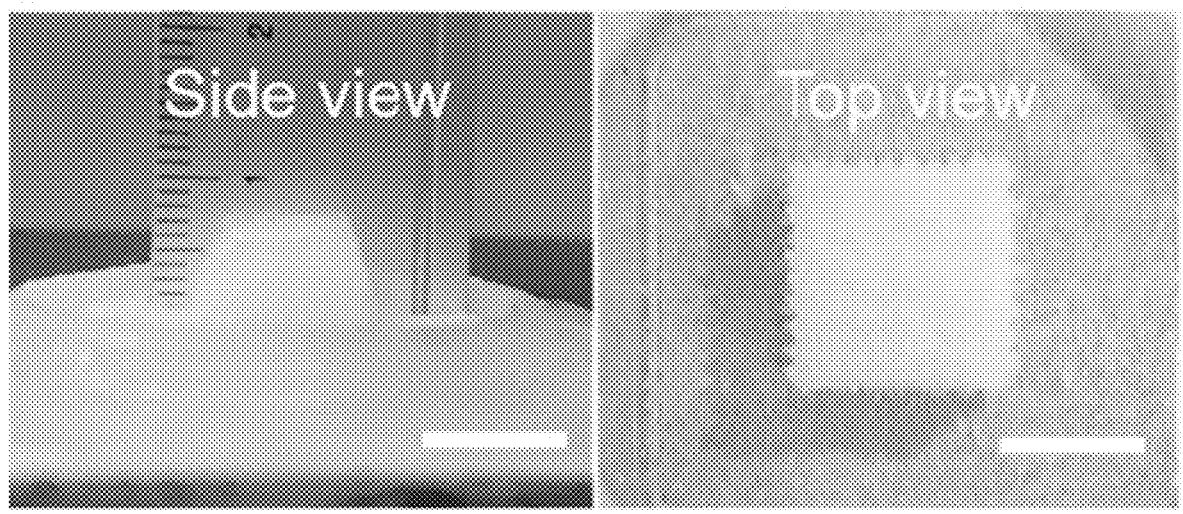
Figure 20C:
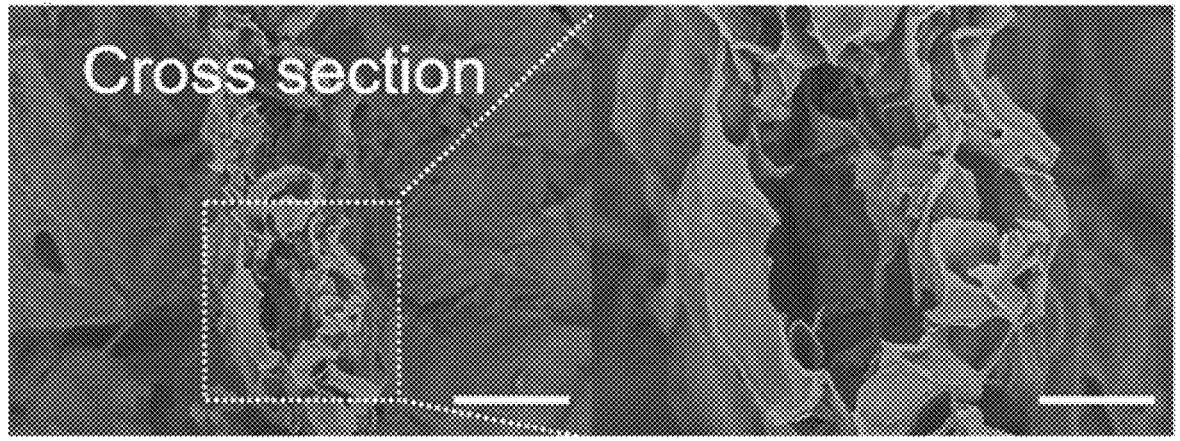
Figure 20D:
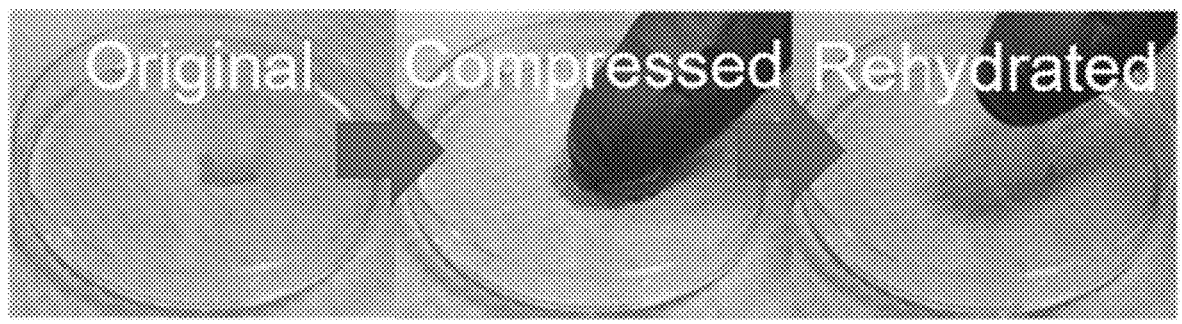

The CSDPU cryogel was 3D-printed after the components of CS and DPU1 was mixed under 4° C. for 4 h (define as "pre-cryogel"). The printing process of CSDPU cryogel is displayed in FIG. 20A. The pre-cryogel was loaded to the syringe of the 3D printer and deposited on the −17° C. platform. By slowing down the crosslink rate, the CSDPU pre-cryogel as ink could be continuously printed through a 210 mm nozzle to produce constructs with the designed three dimensions of 10 mm×10 mm×5 mm (W×D×H), as displayed on FIG. 20B. The final dimensions of the constructs after freeze-drying were *mm×*mm×*mm (~**% shrinkage). The fibers could be stacked up for 24 layers. The SEM image of the cross-section of the construct is shown in FIG. 20C. The shape recovery ability of the construct is displayed in FIG. 20D. The porous structure and shape recovery ability of the cryogel were preserved well after printing. The porosity of the printed cryogel was 92.6%±2.3% and the swelling ratio of the printed cryogel was 3217%±116%.

Figure 21:
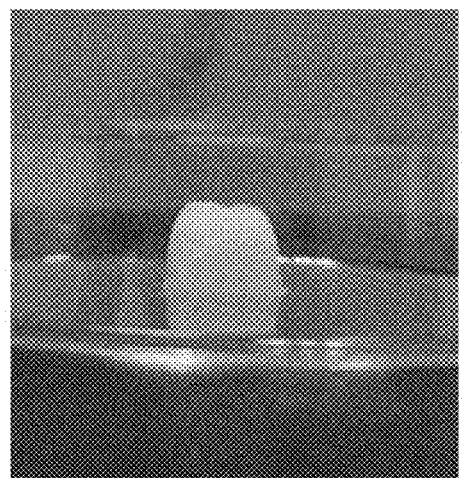
FIG. 21 shows 3D printing of various CSDPU pre-cryogels, made from different DPUs (DPU2, DPU3, and DPU4).

FIG. 21 shows 3D printing of various CSDPU pre-cryogels, made from different DPUs (DPU2, DPU3, and DPU4).

In summary, the crosslinking agent and the hydrogel and cryogel comprising the crosslinking agent of the present invention have the effect on high biocompatibility, adjustable biodegradation rate, no cytotoxicity, simple process, benefit to mass production, environmental protection, environmental responsiveness and drug release, and having self-healing, injectable and shape memory properties.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A biodegradable cryogel obtained by reacting a cross-linking agent comprising a plurality of difunctional polyurethane nanoparticles wherein each of the difunctional polyurethane nanoparticles has a plurality of aldehyde groups with a polymer having amine groups and being placed at a temperature of −17° C. to −25° C.; wherein the polymer having amine groups is chitosan or its derivatives; wherein the biodegradable cryogel upon subcutaneous injection, becomes covered with immune cells on and around it, and wherein said immune cells comprise macrophages, wherein the ratio of M2 macrophages to M1 macrophages is more than three to about 3.5.

2. The biocompatible cryogel according to claim 1, which is prepared by a 3D printing method.

3. The biocompatible cryogel according to claim 1, wherein the biocompatible cryogel has a shape memory property.

4. The biocompatible cryogel according to claim 1, wherein the cryogel is used to culture cells.

5. The biodegradable cryogel according to claim 1, wherein the biocompatible cryogel has a self-healing property.

6. A hydrogel obtained by reacting by reacting a cross-linking agent comprising a plurality of difunctional polyurethane nanoparticles wherein each of the difunctional polyurethane nanoparticles has a plurality of aldehyde groups with a polymer having amine groups; wherein the polymer having amine groups is chitosan or its derivatives; wherein the hydrogel has a storage modulus and a loss modulus, and the storage modulus and the loss modulus are measured by damage-healing cycles at strain of 500% for damage and at strain of 1% for healing; upon subcutaneous injection, becomes covered with immune cells on and around it, and wherein said immune cells comprise macrophages, wherein the ratio of M2 macrophages to M1 macrophages was more than three to about 3.5.

7. The hydrogel according to claim 6, which has a self-healing property.

8. The hydrogel according to claim 6, which is used to culture cells, and is biocompatible.

* * * * *